US006156552A

United States Patent [19]

Okkels et al.

[11] Patent Number: 6,156,552

[45] Date of Patent: Dec. 5, 2000

[54] LIPASE VARIANTS

[75] Inventors: Jens Sigurd Okkels, Vedbæk, Denmark; Shiro Fukuyama, Chiba, Japan; Tomoko Matsui, Chiba, Japan; Tadashi Yoneda, Chiba, Japan

[73] Assignee: Novo Nordisk A/S, Bagsvaerd, Denmark

[21] Appl. No.: 09/251,383

[22] Filed: Feb. 17, 1999

Related U.S. Application Data

[60] Provisional application No. 60/076,463, Mar. 2, 1998.

[30] Foreign Application Priority Data

Feb. 18, 1998 [DK] Denmark ................................ 98-0229

[51] Int. Cl.[7] .......................... C12N 9/20; C07C 15/107; C07C 2/64

[52] U.S. Cl. ......................... 435/198; 435/69.1; 435/183; 435/252.2; 435/320.1; 585/455

[58] Field of Search ................................ 435/198, 252.3, 435/320.1, 69.1; 530/350; 536/23.2, 23.7; 585/455

[56] References Cited

FOREIGN PATENT DOCUMENTS 0 258 068 A2 3/1988 European Pat. Off. .
0 260 105 A2 3/1988 European Pat. Off. .
0 260 105 B1 3/1988 European Pat. Off. .
0 305 216 A1 3/1989 European Pat. Off. .
0 407 225 A1 1/1991 European Pat. Off. .
WO 87/00859 2/1987 WIPO .
WO 92/05249 4/1992 WIPO .
WO 94/01541 1/1994 WIPO .
WO 94/25578 11/1994 WIPO .
WO 95/06720 3/1995 WIPO .
WO 95/14783 6/1995 WIPO .
WO 95/22615 8/1995 WIPO .
WO 95/30744 11/1995 WIPO .
WO 95/35381 12/1995 WIPO .
WO 96/00292 1/1996 WIPO .
WO 96/12012 4/1996 WIPO .
WO 96/27002 9/1996 WIPO .
WO 97/04079 2/1997 WIPO .
WO 97/07202 2/1997 WIPO .
WO 98/08939 3/1998 WIPO .

*Primary Examiner*—Rebecca E. Prouty
*Assistant Examiner*—Manjunath Rao
*Attorney, Agent, or Firm*—Steve T. Zelson; Reza Green; Valeta Gregg

[57] ABSTRACT

The invention provides variant lipases with improved washing performance, including good performance in washing with a detergent having a high content of anionic surfactant at low washing temperature at a short washing time. More particularly, the invention relates to variants of the wild-type lipase from Pseudomonas sp. strain SD 705, deposited as FERM BP-4772.

2 Claims, 10 Drawing Sheets

LIPASE VARIANTS

CROSS-REFERENCE TO RELATED APPLICATIONS

This application claims priority under 35 U.S.C. 119 of Danish application 98 00229, filed Feb. 18, 1998, and U.S. provisional application Ser. No. 60/076,463, filed Mar. 2, 1998, the contents of which are fully incorporated herein by reference.

FIELD OF THE INVENTION

The present invention relates to lipase variants of particular interest for use in detergent or cleaning compositions. More particularly, the invention relates to variants of the wild-type lipase from Pseudomonas sp. strain SD 705, deposited as FERM BP-4772.

BACKGROUND OF THE INVENTION

For a number of years lipases have been used as detergent enzymes to remove lipid or fatty stains from clothes and other textiles, particularly a lipase derived from *Humicola lanuginosa* (EP 258 068 and EP 305 216) sold under the tradename Lipolase®. WO 95/06720 and WO 96/27002 describe a wild-type lipase from Pseudomonas sp. strain SD 705, its amino acid sequence and DNA sequence and its use in detergents. Other Pseudomonas lipases have also been suggested as detergent enzymes, e.g. lipase from *P. pseudoalcaligenes* (WO 87/00859) and *P. wisconsinensis* (WO 96/12012).

In recent years attempts have been made to prepare lipase variants having improved properties for detergent purposes. Such lipase variants are described in WO 92/05249, WO 94/01541, EP 407 225, EP 260 105, WO 95/35381, WO 96/00292, WO 95/30744, WO 94/25578, WO 95/14783, WO 95/22615, 97/04079 and WO 97/07202.

There is an ever existing need for providing novel lipases with improved properties, in particular improved washing properties. The present invention relates to such novel lipases.

SUMMARY OF THE INVENTION

The invention provides variant lipases with improved washing performance, including good performance in washing with a detergent having a high content of anionic surfactant at low washing temperatures within a short washing time.

In one aspect, the invention provides a lipase which is a variant of a mature, wild-type lipase derived from Pseudomonas sp. strain SD 705 (FERM BP-4772). The variant has an amino acid sequence having more than 85% identity with said wild-type lipase and comprises a modification which is:

a) substitution of S3, T7, Q10, T16, M19, L20, D22, S23, L24, L25, D29, W31, Y32, G33, S36, A37, R39, K40, T44, Y46, T48, E49, S51, Q52, L53, D54, T55, A58, E61, Q62, L64, T65, V67, E68, E69, 170, V71, I73, S74, K76, P77, F82, H86, G88, 191, Y93, V94, A96, V97, G109, A110, P111, H112, A116, T117, F120, 1121, Q123, E126, A129, S130, A132, 1133, L134, A135, G136, V138, G140, L144, F147, S153, D154, T155, S159, L160, G161, T162, E164, S165, N167, S168, E169, A171, A172, R173, F174, A176, F178, Q180, P183, A186, G188, E189, G190, D191, Y192, N195, V197, S203, T205, S206, P207, L208, P214, S215, L217, L218, G220, A221, S223, T225, F228, A230, R237, S240, R241, M244, R247, N249, R251, L255, E257, V258, Q260, T261, L264, T265, S266, 1267, F268, E269, T270, S271, S274, V275, R277, Q278, Q279, A286, G287 or L288 with a different amino acid residue or b) insertion of one or more amino acid residues before Gl, between G27 and V28, between V124 and P125, between S185 and A186, between A186 and C187, between V193 and V194, between G196 and V197, or between V197 and R198, or c) deletion of F1, G2, S3, S4, 173, S74, S153, D154, T155, L264, T265, S266, 1267, F268 or E269.

d) a peptide addition at the N-terminal or C-terminal.

The invention also provides a DNA construct encoding the lipase, an expression vector harboring the DNA construct, a transformed host cell containing the DNA construct or the expression vector, a method of producing a lipase by culturing the host cell so as to produce the lipase and recovering the lipase from the resulting broth.

The invention further provides a method of constructing a lipase which is a variant of a mature, wild-type lipase from Pseudomonas sp. strain SD 705 (FERM BP-4772), having an improved wash performance as compared to the parent lipase, which method comprises:

a) subjecting one or more of the following amino acid subsequences of the parent lipase to localized random mutagenesis: G2-G27, V28-D54, E57-N80, K78-P99, A103-P115, R122-S149, S153-F178, P179-S203, S206-L234, G233 -T261 and L264-L288, b) expressing the variety of mutated DNA sequences originating from the parent lipase obtained in step (a) in suitable host cells; and c) screening for host cells expressing a mutated lipase which has a decreased dependence on calcium and/or an improved tolerance towards a detergent or a detergent component as compared to the parent lipase.

Finally, the invention provides a detergent composition comprising a surfactant and said lipase or produced according to either of said methods.

DETAILED DESCRIPTION OF THE INVENTION

Parent lipase

Figure 1:
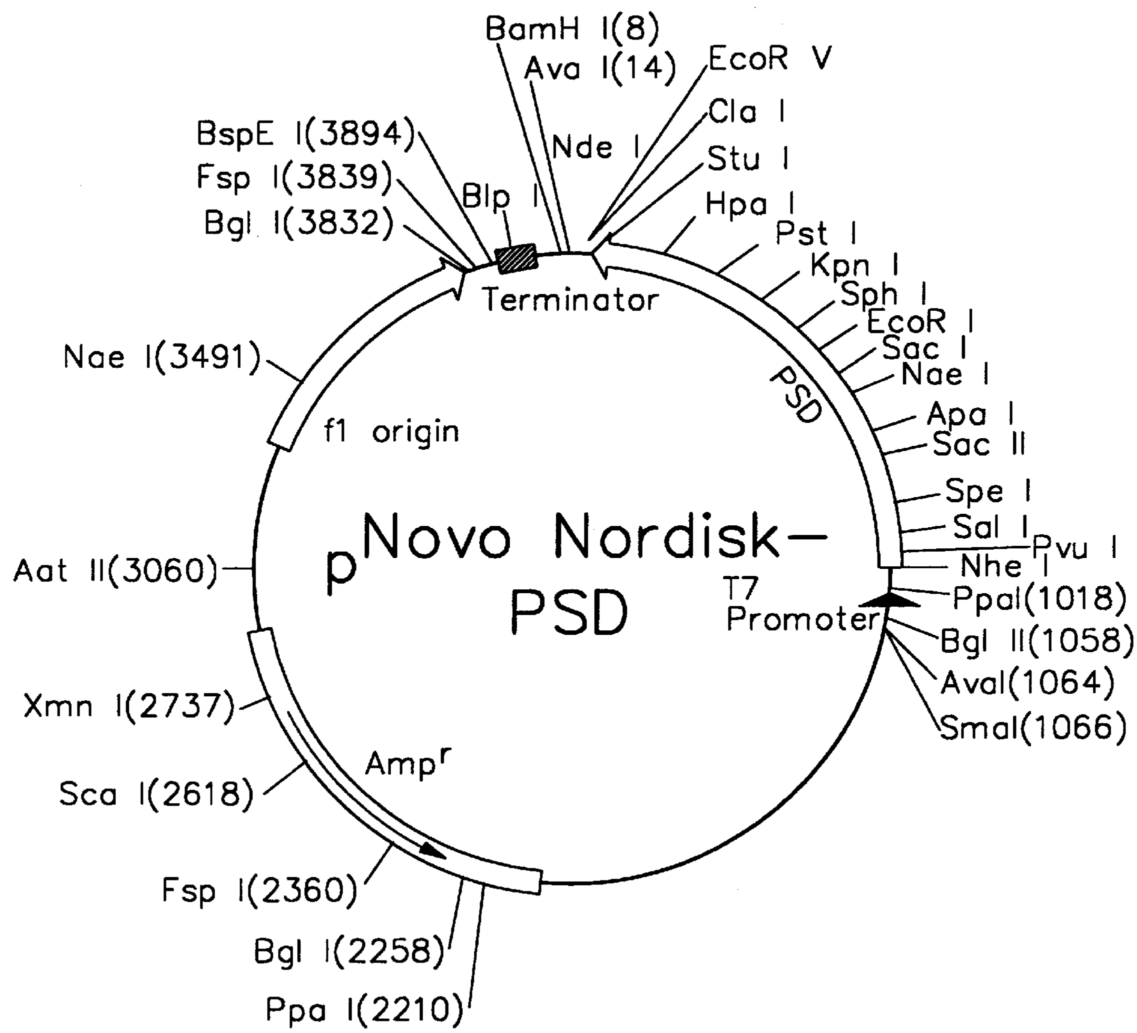
FIG. 1 shows a restriction map of pNovoNordisk-PSD.

The mature, wild-type lipase derived from Pseudomonas sp. strain SD 705 (FERM BP-4772) is described in WO 95/06720 (EP 721 981) and WO 96/27002 (EP 812 910). It has the amino acid sequence shown in sequence listing No. 1 of WO 96/27002. In this specification, it is also referred to as Liposam™ or simply as wt (for wild-type).

Lipase variants

The nomenclature used herein for defining modifications is as described in WO 92/05249. For instance, S3Y indicates that the serine residue (S) located in position 3 of the mature parent lipase is replaced with a tyrosine residue (Y). −1AS indicates that AS is inserted at position −1, i.e. before F1 at the N-terminal. D154* indicates deletion of D at position 154. V193VHNVR indicates that V at position 193 is substituted with VHNVR.

When the amino acid residue to be replaced is an E or a D, it is preferably replaced with any of the hydrophobic amino acid residues W, V, F, Y, I, L, A, any of the positively charged amino acid residues R, K or H, or any of the neutral amino acid residues S, T, G or Q.

In a preferred embodiment, the modification is:

a) substitution of S3, T7, Q10, T16, M19, L24, W31, Y32, S36, K40, T44, Y46, T48, S51, Q52, L53, E61, L64, T65, V67, E68, I70, V71, F82, Y93, V94, V97, P111, A116, T117, F120, I121, S130, L134, G136, V138, G140, L144, F147, L160, T162, E169, R173, F174, F178, Q180, A186, G188, E189, N195, V197, S206, P207, L208, P214, S215, L218, G220, A221, T225, A230, R237, R241, L255, E257, V258, Q260, T261, L264, T265, S266, I267, E269, T270, S274, V275, R277, Q278, Q279, A286, G287 or L288 with a hydrophobic and/or positively charged amino acid residue, or b) insertion of a hydrophobic and/or positively charged amino acid residue between V124 and P125, between A186 and C187, between V193 and V194 or between V194 and N 195.

The hydrophobic or positively charged amino acid is preferably R, K, W, F, Y, I, L, H, A or V.

In a more preferred embodiment the modification is:

a) the substitution S3Y, T7A, Q10K, T16V, M19V, L20T, D22N, S23T, L241, L25G, D29N, W31 F, Y32H, G33T, S36W, A37N, R39E, K40R, T44R, Y46H, T48A, E49S, S51A, Q52A, L53F, D54N, T55D, A58Q, E61A, Q62E, L64A, T65R, V671, E68V, E69P, 170W, V71A, 173G, S74G, K76G, P77G, F821, H86Q, G88S, 191S, Y93V, V94A, A96S, V97L, G109N, A11OG, PllV, H112N, A116K, T117V, F12OV, 1121V, Q123G, E126P, A129G, S1301, S130P, A132G, 1133G, L134A, A135N, G136A, V138A, G140A, L144V, F147L, S153N, D154N, T155N, S159G, L1601, G161N, T162A, E164G, S165T, N167T, S168T, E169A, A171T, A172S, R173A, F174L, A176S, F178H, Q180H, P183N, A186S, A186Y, G188A, E189K, G190S, D191T, Y192E, N195R, V197H, V197S, V1971, S203T, T205N, S206A, P207A, L208Y, P214A, S215A, L217P, L218F, G220A, A221F, S223G, T225V, F228S, A230K, R237V, S240T, R241Y, M244Q, R247D, N249S, R251N, L255V, E257A, V2581, Q260H, T261L, L2641, T265R, S266G, 1267W, F268W, T2701, S271E, S274F, V275L, R277H, Q278H, Q279H, A286K, G287A or L288V, or b) substitution of Al 86 with SY, or of V1 97 with HSI, or c) insertion of L between G27 and V28, of L between V124 and P125, or of HN between V193 and VI 94.

The peptide addition at the C-terminal and/or the N-terminal may be an extension as disclosed in WO 97/04079, e.g. the extension SPIRR or SPIRPRP at the N-terminal. In addition to or instead of this extension, a short extension such as AS may also be attached at the N-terminal. Thus, a preferred peptide addition is AS, ASPIRPRP OR ASPIRR attached to the N-terminal.

The variant lipase of the invention preferably has two or more of said modifications. Some preferred variants with multiple modifications are:

a) −1AS, M19V, F228S, A230K, b) −1AS, M19V, E257A, V2581, Q260H, T261L c) −1ASPIRPRP, E257A, V2581, Q260H, T261L d) −LASPIRPRP, Al86SY, E257A, V2581, Q260H, T261L

The variant lipase of the invention may comprise a substitution at or near the calcium binding site, e.g. a substitution of Q262. The static environment around calcium binding may also be influenced by substitution of E259.

Furthermore, the variant lipase of the invention may include other modifications of the parent enzyme, in addition to those discussed above. Thus, the lipase variant may be truncated by deleting amino acid residues corresponding to the first 1, 2, 3, 4, 5 or 6 positions at the N-terminal. The total number of modifications compared to Liposam is preferably more than 2, e.g. more than 5, and preferably less than 20, e.g. less than 15, particularly less than 10. The amino acid sequence of the variant lipase preferably has an identity with Liposam of more than 90%, e.g. more than 95%, particularly more than 98%.

The identity of two polypeptides may be determined as the degree of identity between the two sequences, indicating a derivation of the first sequence from the second. The identity may suitably be determined by means of computer programs known in the art such as GAP provided in the GCG program package (Needleman, S. B. and Wunsch, C. D., (1970), Journal of Molecular Biology, 48, 443–453. Using GAP with the following settings for polypeptide sequence comparison: GAP creation penalty of 3.0 and GAP extension penalty of 0.1.

In accordance with the invention, it is also contemplated to apply, to the lipase variant, one or more charged amino acids which permit effective purification of the enzyme. Techniques for doing this are well known to a person skilled in the art of molecular biology.

DNA sequence

The DNA sequence encoding the lipase variant may suitably be prepared by introducing the relevant modifications in a cDNA or genomic DNA sequence encoding the parent lipase. The modifications may be introduced in accordance with well-known techniques such as those disclosed by Sambrook et al. The DNA construct may further comprise control sequences necessary for achieving expression of the modified DNA sequence. The control sequence may be an appropriate promoter sequence, a nucleic acid sequence which is recognized by a host cell for expression of the nucleic acid sequence. The promoter sequence contains transcription and translation control sequences which mediate the expression of the first wash lipolytic enzyme. The promoter may be any nucleic acid sequence which shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the lipase variant. The terminator sequence may be native to the nucleic acid sequence encoding the lipase variant or may be obtained from foreign sources.

The control sequence may also be a suitable leader sequence, a polyadenylation sequence, a signal peptide encoding sequence, or any other transcriptional or translational regulatory sequence. In addition, the DNA construct may comprise a DNA sequence encoding a factor necessary for producing the lipase variant in active form, a so-called lipase modulator or chaperone, cf. WO 91/00908, WO 93/13200 and EP 331 376.

Expression vector

The expression vector of the invention may comprise control sequences as described above necessary for the proper expression of the DNA sequence encoding the lipase variant of the invention. The choice of expression vector will depend, e.g., on the host cell intended for use in the production of the lipase. Suitable expression vectors are disclosed, e.g., in WO 91/00908, WO 93/13200, EP 331 376 and WO 95/14783.

Host cell

The host cell is preferably a cell of a Pseudomonas sp. such as *Ps. pseudoalcaligenes,* or a cell of *E. coli.* In particular, the host cell may be any of the host cells disclosed in WO 91/00908, WO 93/13200, EP 331 376, WO 95/20744 and WO 95/14783.

If no lipase modulator gene is present on the DNA construct or the expression vector of the invention, it is desirable that such gene is present in and capable of being expressed from the host cell of choice so as to enable the production of an active lipase variant from said host cell.

When the host cell is a cell of a Pseudomonas sp. it may be desirable that any native lipase gene of such cell is inactivated or deleted. Such inactivation or deletion may be performed in accordance with well-known methods, e.g. as disclosed in WO 95/20744 and WO 9514783. A suitable lipase negative Pseudomonas host cell is the *Ps. alcaligenes* PS600 described in WO/9530744 or the lipase negative *Ps. mendocina* strain LD9 described in WO 95/14783.

The host cell used for transformation is preferably a cell of E. coli or a cell of a Pseudomonas sp., in particular a lipase negative strain of a Pseudomonas sp. Production of lipase The host cells may be cultivated in a nutrient medium suitable for production of the lipase variant using methods known in the art. For example, the cell may be cultivated by shake flask cultivation, small-scale or large-scale fermentation (including continuous, batch, fed-batch, or solid state fermentation) in laboratory or industrial fermentors performed in a suitable medium and under conditions allowing lipase variant to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, More Gene Manipulations in Fungi, Academic Press, Calif., 1991). Suitable media are available from commercial suppliers or may be prepared according to published compositions (e.g., in catalogues of the American Type Culture Collection). If the lipase variant is secreted into the nutrient medium, the variant can be recovered directly from the medium. If the variant is not secreted, it is recovered from cell lysates.

The resulting lipase variant may be recovered by methods known in the art. For example, the variant may be recovered from the nutrient medium by conventional procedures including, but not limited to, centrifugation, filtration, extraction, spray-drying, evaporation, or precipitation. The recovered variant may then be further purified by a variety of chromatographic procedures, e.g., ion exchange chromatography, gel filtration chromatography, affinity chromatography, or the like.

The lipase variant of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J. -C. Janson and Lars Ryden, editors, VCH Publishers, New York, 1989).

If no lipase modulator is expressed by the host cell of choice such modulator may be added to the isolated lipase protein or an active lipase may be obtained by use of any other of the methods disclosed in WO 93/13200 or WO 91/00908.

Second Pseudomonas lipase

As described above, the invention provides a method of preparing a lipase variant from Liposam and a second lipase which shows a high degree of identity with Liposam on the amino acid or the structural level. More specifically, the identity is at least 40%, e.g. at least 60%, such as at least 80% or at least 90%.

The second lipase may in particular be a lipase from Pseudomonas, e.g. from *Ps. aeruginosa,* such as strains EF2, PACLR, PAO1, TE3285; *Ps. cepacia,* such as strain M-12-33 or DSM 3959; *Ps. fragi,* such as strains IFO 3458 or IFO 12049; *Ps. glumae; Ps. mendocina,* such as strain SD702; *Ps. pseudoalcaligenes,* such as strain M1 (EP 334,462); *Ps. wisconsinensis* (WO 96/12012); and other strains of Pseudomonas sp., such as ATCC 21808,109, or KWI-56. Reference is made to Gilbert, E. J., (1993), *Pseudomonas lipases:* Biochemical properties and molecular cloning. Enzyme Microb. Technol., 15, 634–645. The species *Pseudomonas cepacia* has recently been reclassified as *Burkholderia cepacia,* but is termed *Ps. cepacia* in the present application.

The two amino acid sequences can be aligned by known computer programs like GAP or MegAlign (DNASTAR) to identify sequences with more than 40% identity. Substitutions, deletions and/or insertions are then identified based on the differences between the two lipases in the alignment. One or more of the identified substitutions, insertions and deletions can be introduced into the gene encoding Liposam by site-directed mutagenesis method or by hybrid gene construction using methods known in the art. The resulting lipase gene may be expressed in *E. coli*, Pseudomonas, Bacillus, Aspergillus or another suitable expression organism and the lipase may be purified and tested for improved wash activity. A number of variants should be tested to find the ones improved in wash tests.

Preferably, this method may be used to introduce substitutions, deletions and insertions from a second lipase with a superior wash performance into Liposam to improve the wash performance of the latter.

The substitutions, deletions and/or insertions to be introduced may advantageously be chosen in the subsequences described above in relation to random mutagenesis. It is preferred to introduce two or more such changes, e.g. three or four changes. Additionally, the variant amino acid sequence may also include the N-terminal or C-terminal extensions described above, the sequence may further be subjected to random mutagenesis as described above, and the sequence may additinoally include one or more of the substitutions, deletions or insertions described earlier in this specification.

The lipase variant may be a hybrid of the two lipases, comprising an N-terminal subsequence of one lipase combined with a C-terminal subsequence of the second lipase. Such hybrid lipases may be prepared by methods known in the art, e.g. by module shift using synthetic genes as described in the examples. The hybrid lipases may advantageously include the N-terminal or C-terminal extensions described above.

Liposam has an amino acid identity of 83% with the M1 lipase, and 45% with the *Ps. wisconsinensis* lipase.

Random mutagenesis

As described above, the invention provides construction of a variant of Liposam by a method comprising:

a) subjecting one or more specified amino acid subsequences of the parent lipase to localized random mutagenesis, b) expressing the variety of mutated DNA sequences originating from the parent lipase obtained in step (a) in suitable host cells; and c) screening for host cells expressing a mutated lipase which has a decreased dependence on calcium and/or an improved tolerance towards a detergent or a detergent component as compared to the parent lipase.

Random mutagenesis indicates the introduction of one or more modifications at random positions of the parent enzyme or introduction of random amino acid residues in selected positions or regions of the parent enzyme. It may be carried out as localized random mutagenesis, i.e. random mutagenesis conducted of a specific limited part of the parent enzyme. The random mutagenesis is normally accompanied by a screening which allows the selection of mutated lipolytic enzymes which, as compared with the parent enzyme, have improved properties. Suitable techniques for introducing random modifications and screening for improved properties are described in WO 95/22615.

The localized random mutagenesis performed in step (a) may be essentially as described in WO 95/22615. A preferred method is to use doped or spiked oligonucleotides for the mutagenesis. An example of a doping scheme is given in the Examples hereinafter.

The host cell to be used for expression in step (b) is preferably a cell of *E. coli.*

Preferably, the screening of step (c) is performed for improved tolerance towards an anionic surfactant such as an alkyl sulfate or LAS or a detergent, e.g. the PCS detergent described in the Materials and Methods section herein. The screening is preferably performed by a so-called filter assay, e.g. as described in the Materials and Methods section herein.

It will be understood that once a host cell comprising a mutated DNA sequence encoding a lipase variant with improved wash performance has been identified by the screening step c), the DNA sequence may be isolated from the host cell, and transformed into another host cell to be used for the recombinant production of the lipase variant. Subsequently, the lipase variant may be prepared and recovered as described hereinbefore.

Lipase properties

The lipase of the invention preferably has improved wash performance as compared to the parent enzyme, i.e. an improved performance when tested in a suitable wash assay or a wash related assay, e.g. as described in this specification or in WO 97/04079 or WO 97/07202. The improved performance may be in terms of lipid stain removing capability and/or a decreased calcium dependency, an improved tolerance towards a detergent or detergent component, an increased hydrophobicity, an interesting substrate specificity, an improved one-cycle wash effect, etc.

The lipase preferably exhibits enzymatic activity towards lipase substrates having hydrocarbon chains (ffa-part) of a length exceeding approx. 6–8 C-atoms.

The lipase of the invention preferably has a decreased dependence on calcium, i.e. it requires lower amounts of Ca2+ for exhibiting the same degree of activity and/or stability as the parent enzyme when tested under similar conditions. In other words the stability and/or activity of the mutated enzyme is/are increased in the absence of calcium as compared to that of the parent enzyme. The stability may, e.g., be assayed by a determination of residual activity upon preincubation under Ca-free conditions and/or DSC (Differential Scanning Calorimetry) in the absence/presence of free Ca2+. Preferably, the mutated lipase of the invention is substantially independent of the presence of calcium for exhibiting enzymatic activity, in particular at a pH higher than 8.

The lipase of the invention preferably has an improved tolerance towards a detergent or detergent component, i.e. it is active at higher concentrations of the detergent or detergent component than the parent enzyme.

The detergent can be a mixture of detergent ingredients normally used for washing or dishwashing. Analogously, the detergent component can be a component or ingredient normally found in detergent or dishwashing compositions, specific examples of which are given in the section further below entitled "Detergent compositions".

Lipase activity (LU)

A substrate for lipase was prepared by emulsifying glycerin tributyrate (MERCK) using gum Arabic as emulsifier. Lipase activity is assayed at pH 7 using pH stat method. One unit of lipase activity (LU) is defined as the amount needed to liberate one micromole fatty acid per minute.

Detergent additive

According to the invention, the lipase may typically be used as an additive in a detergent composition. This additive is conveniently formulated as a non-dusting granulate, a stabilized liquid, a slurry or a protected enzyme. Non-dusting granulates may be produced, e.g., as disclosed in U.S. Pat. No. 4,106,991 and U.S. Pat. No. 4,661,452 (both to Novo Industri A/S) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

A suitable activity range for a detergent additive containing the lipolytic enzyme of this invention is 5,000–100,000 OPIDU/g (OPID measured at pH 9) or 0.01–100 mg pure enzyme protein per g of the additive.

DETERGENT DISCLOSURE AND EXAMPLES

The detergent composition of the invention comprises the lipase of the invention and a surfactant. Additionally, it may optionally comprise a builder, another enzyme, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or nonencapsulated perfumes.

The detergent composition according to the invention can be in liquid, paste, gels, bars or granular forms. The pH (measured in aqueous solution at use concentration) will usually be neutral or alkaline, e.g. in the range of 7–11.

The lipase of the invention, or optionally another enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

The detergent composition of the invention may comprise the lipase in an amount corresponding to 10–50,000 LU per gram of detergent, preferably 20–5,000 LU/g. The detergent may be dissolved in water to produce a wash liquor containing lipolytic enzyme in an amount corresponding to 25–15,000 LU per liter of wash liquor. The amount of lipase protein may be 0.001–10 mg per gram of detergent or 0.001–100 mg per liter of wash liquor.

Surfactant system

The surfactant system may comprise nonionic, anionic, cationic, ampholytic, and/or zwitterionic surfactants. The surfactant system preferably consists of anionic surfactant or a combination of anionic and nonionic surfactant, e.g. 50–100 % of anionic surfactant and 0–50 % nonionic. The laundry detergent compositions may also contain cationic, ampholytic, zwitterionic, and semi-polar surfactants, as well as the nonionic and/or anionic surfactants other than those already described herein.

The surfactant is typically present at a level from 0.1% to 60% by weight. Some examples of surfactants are described below.

Nonionic surfactant

The surfactant may comprise polyalkylene oxide (e.g. polyethylene oxide) condensates of alkyl phenols. The alkyl group may contain from about 6 to about 14 carbon atoms, in a straight chain or branched-chain. The ethylene oxide may be present in an amount equal to from about 2 to about 25 moles per mole of alkyl phenol.

The surfactant may also comprise condensation products of primary and secondary aliphatic alcohols with about 1 to about 25 moles of ethylene oxide. The alkyl chain of the aliphatic alcohol can either be straight or branched, and generally contains from about 8 to about 22 carbon atoms.

Further, the nonionic surfactant may comprise polyethylene oxide condensates of alkyl phenols, condensation products of primary and secondary aliphatic alcohols with from about 1 to about 25 moles of ethylene oxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium.

Other anionic surfactants include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates.

Alkylbenzene sulfonates are suitacble, especially linear (straight-chain) alkyl benzene sulfonates (LAS) wherein the alkyl group preferably contains from 10 to 18 carbon atoms.

The laundry detergent compositions typically comprise from about 1% to about 40%, preferably from about 3% to about 20% by weight of such anionic surfactants.

Builder system

The compositions according to the present invention may further comprise a builder system. Any conventional builder system is suitable for use herein including aluminosilicate materials, silicates, polycarboxylates and fatty acids, materials such as ethylenediamine tetraacetate (EDTA), metal ion sequestrants such as aminopolyphosphonates. Phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Detergency builder salts are normally included in amounts of from 5% to 80% by weight of the composition. Preferred levels of builder for liquid detergents are from 5% to 30%.

Other enzymes

The detergent composition may, in addition to the lipase of the invention, comprise other enzyme(s) providing cleaning performance and/or fabric care benefits, e.g. proteases, lipases, cutinases, amylases, cellulases, peroxidases, oxidases (e.g. laccases).

Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279) and variants thereof.

Bleaching agents:

The detergent composition (especially in the case of a granular detergent) may also comprise a bleaching agents, e.g. an oxygen bleach or a halogen bleach. The oxyugen bleach may be a hydrogen peroxide releasing agent such as a perborate (e.g. PB1 or PB4) or a percarbonate, or it may e.g. be a percarboxylic acid. The particle size may be 400–800 microns. When present, oxygen bleching compounds will typically be present at levels of from about 1% to about 25%.

The hydrogen peroxide releasing agent can be used in combination with bleach activators such as tetraacetylethylenediamine (TAED), nonanoyloxybenzenesulfonate (NOBS), 3,5-trimethyl-hexsanoloxybenzenesulfonate (ISONOBS) or pentaacetylglucose (PAG).

The halogen bleach may be, e.g. a hypohalite bleaching agent, for example, trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

More specifically, the lipase of the invention may be incorporated in the detergent compositions described in WO 97/04079, WO 97/07202, WO 97/41212, and PCT/DK 97/00345.

EXAMPLES

Strains and plasmids

Figure 2:
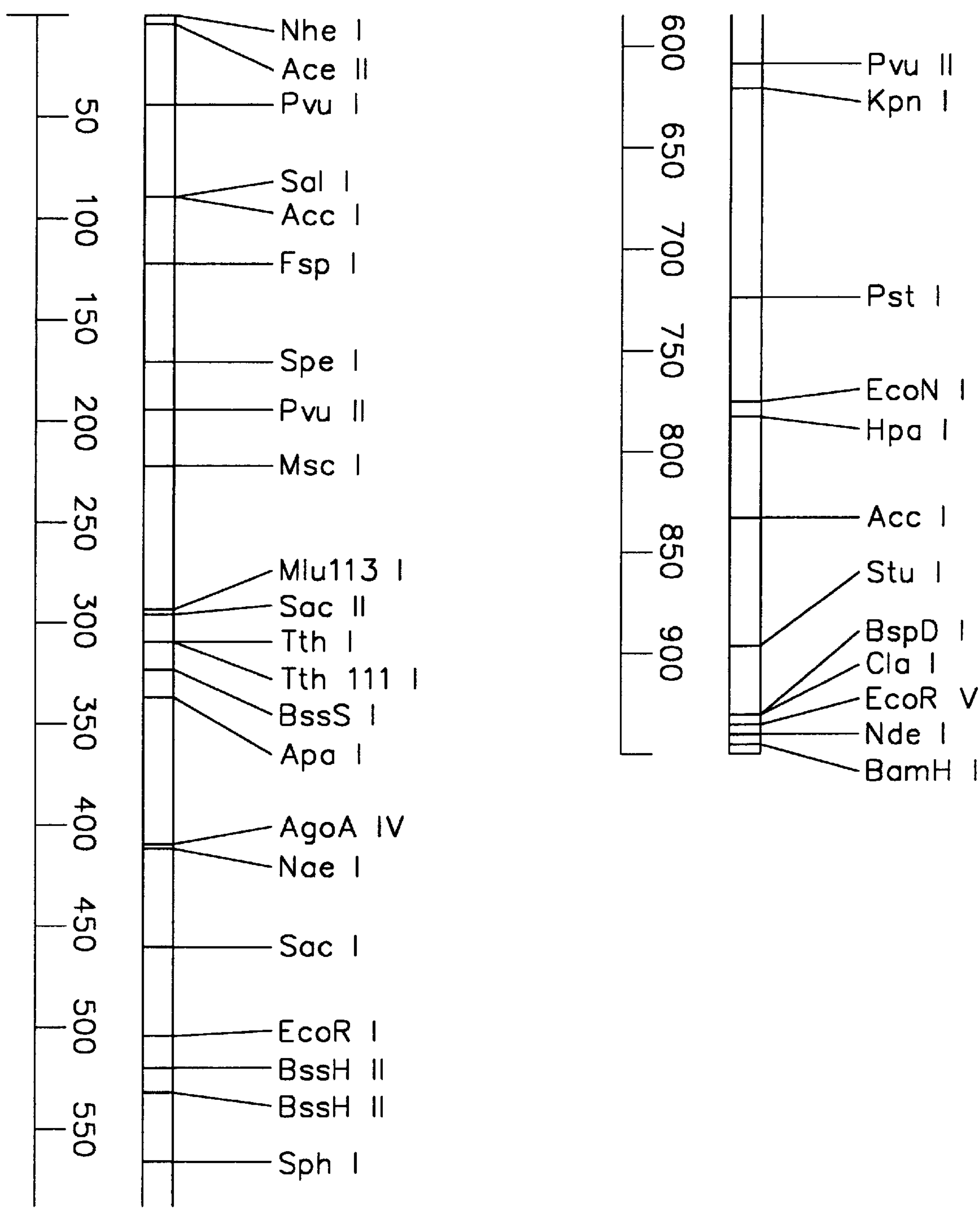
FIG. 2 shows a restriction map of the synthetic gene shown in SEQ ID NO: 13.

*E. coli* DH12S is available from Gibco.

pTrc99A is available from Pharmacia.

pNOVO NORDISK PSD is shown in FIG. 1. It was prepared by inserting a synthetic gene into a modified T7 vector where restriction sites have been removed and other sequences removed. The modified T7 vector has Xba I and Bam Hi sites at the beginning, and the Xba I site is removed by oligo insertion when introducing the gene. The synthetic gene is shown in SEQ ID NO: 13; it encodes Liposam. A restriction map of the gene is shown in FIG. 2.

*Pseudomonas mendocina* SD702 is described in JP-A 6-38746 and the equivalent U.S. Pat. No. 5,454,971.

pMFY42 is a broad host range plasmid constructed from pMFY40 (Fukuda, M. and Yano, K (1985) Agric. Biol. Chem. 49 (9), 2719–2724) by replacing the Ampicillin resistance gene with a kanamycin resistance gene as described by Fukuda (1990), Iden, 4 11), 53–58.

*Pseudomonas mendocina* LDMI is a lipase deficient derivative of *P. mendocina* SD702, prepared as follows. The 800 bp region upstream from the SD702 lipase gene (region A) was obtained by a PCR amplification using the primers IN1 and IN2. The 1200 bp region downstream of the SD702 lim gene (region B) was also PCR amplified using the primers IN3 and IN4. These two fragments were cloned next to each other and introduced into the pMFY42 plasmid. The resulting plasmid was transformed into the SD702 strain and selected for by tetracyclin. Due to the identity with either region A or B the plasmid was expected to recombine into the SD702 strains chromosome at one of these two locations. When integrated into the chromosome the plasmid may recombine out again either by leaving the same configuration as in the wt SD702 strain or by deleting the lipase and lim gene in the SD702 strain. The last case was screened for by loss of both tetracyclin resistance and lipase activity. Four strains were obtained with loss of both the tetracyclin resistance and lipase activity and one of them named LDM1. It was confirmed by PCR that the strain had lost both the lipase and lim gene.

pUC119 is available from Takara.

Figure 3:
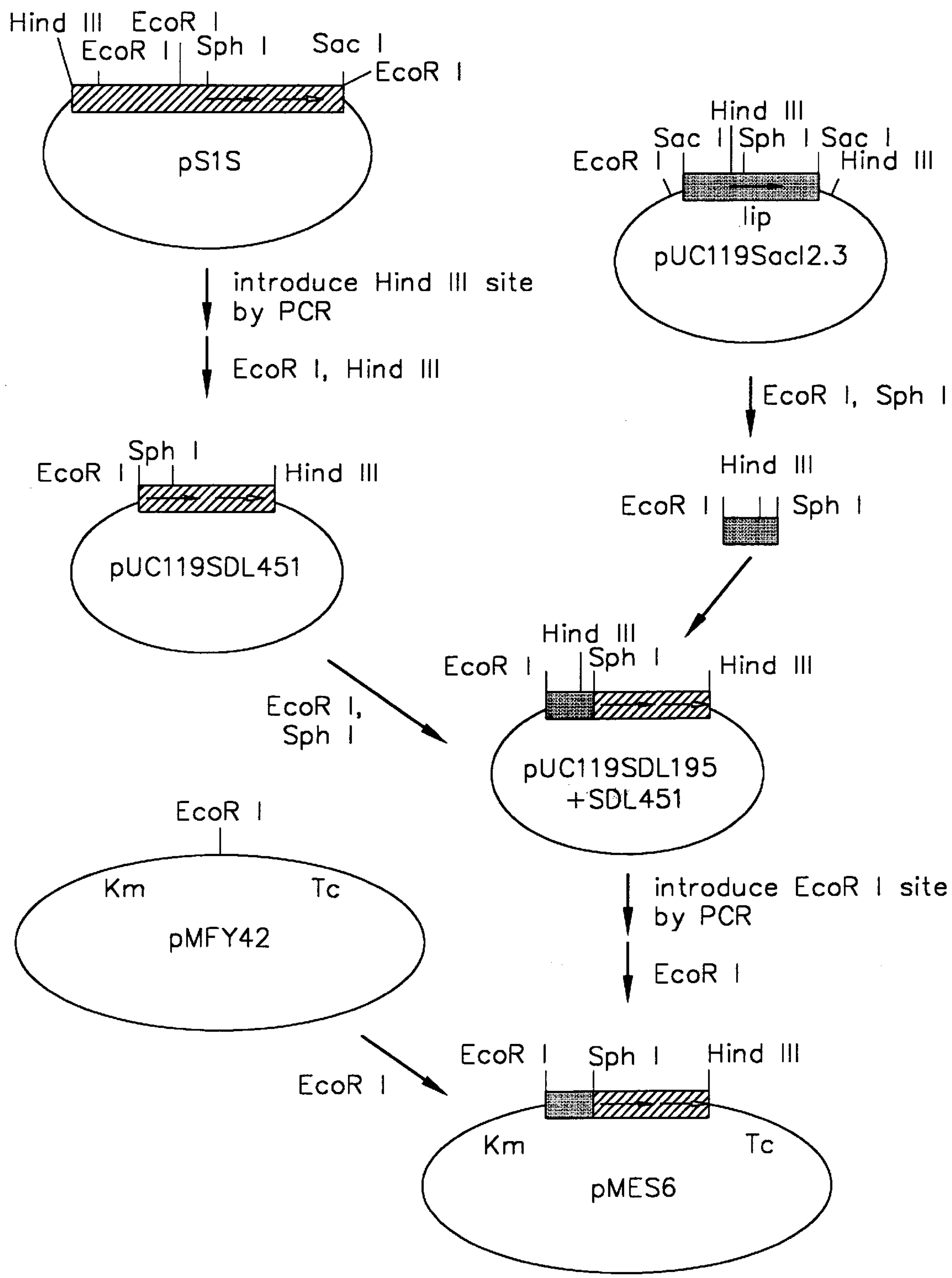
FIG. 3 shows the construction of pUC1 19SDL195+SDL451 and of pMES6.

*E. coli* JM101 is available from TAKARA.

pS1S, including Liposam gene and Liposam lim gene is described in JP-A 8-228778.

pUC119Sac2.3, including 2.3kbp of Sac I fragment containing *P. mendocina* SD702 lipase gene, is described in JP-A 7-143883.

pUC119SDL195+SDL451 is constructed from pS1S and pUC119Sac2.3 as shown in FIG. 3.

Figure 4:
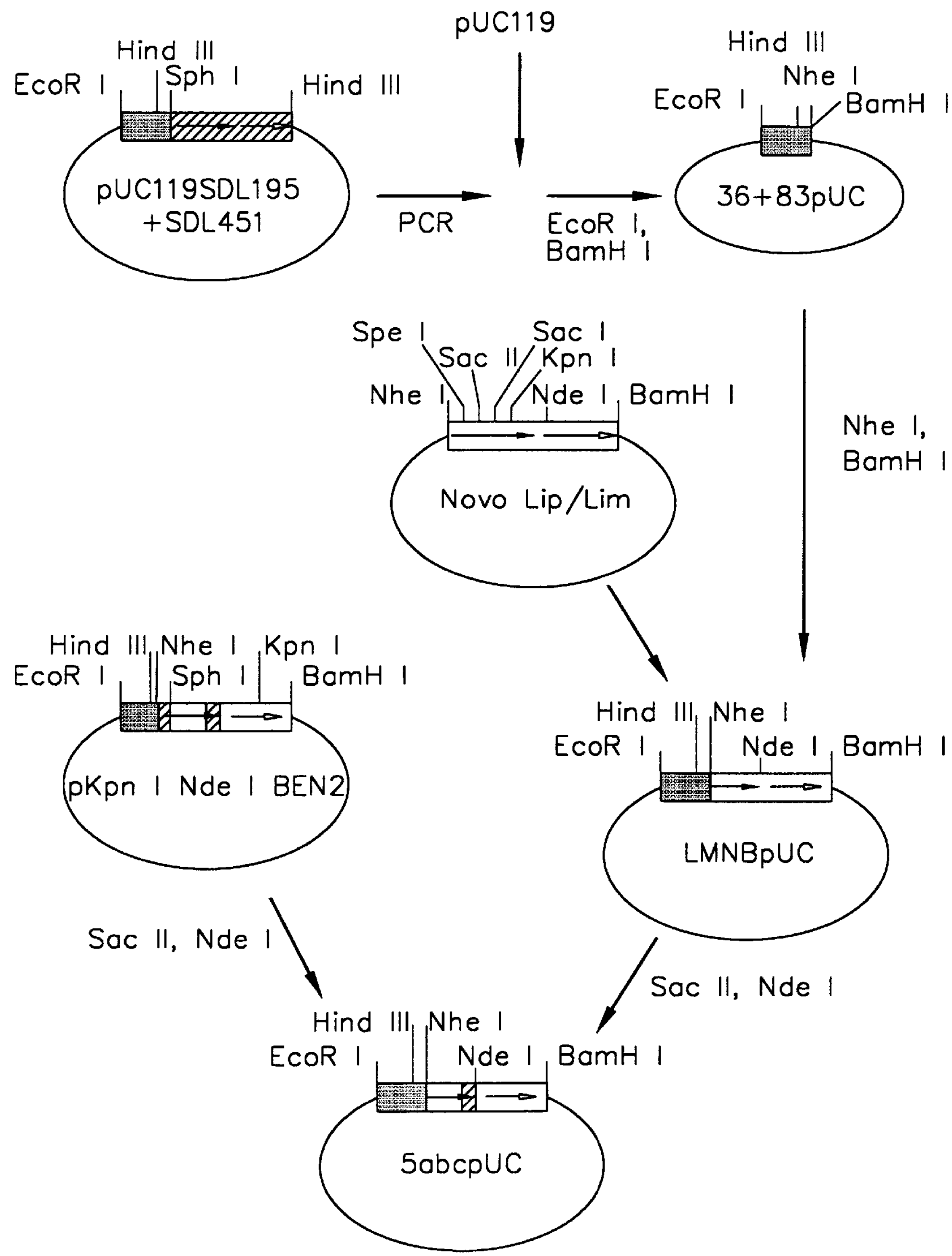
FIG. 4 shows the construction of 36+83pUC and LMN-BpUC.

36+83pUC, containing SD702 lipase promoter region and the cloning sites for Nhe I-Bam HI fragment is constructed from pUC119SDL195+SDL451 and pUC119, as shown in FIG. 4.

Figure 6:
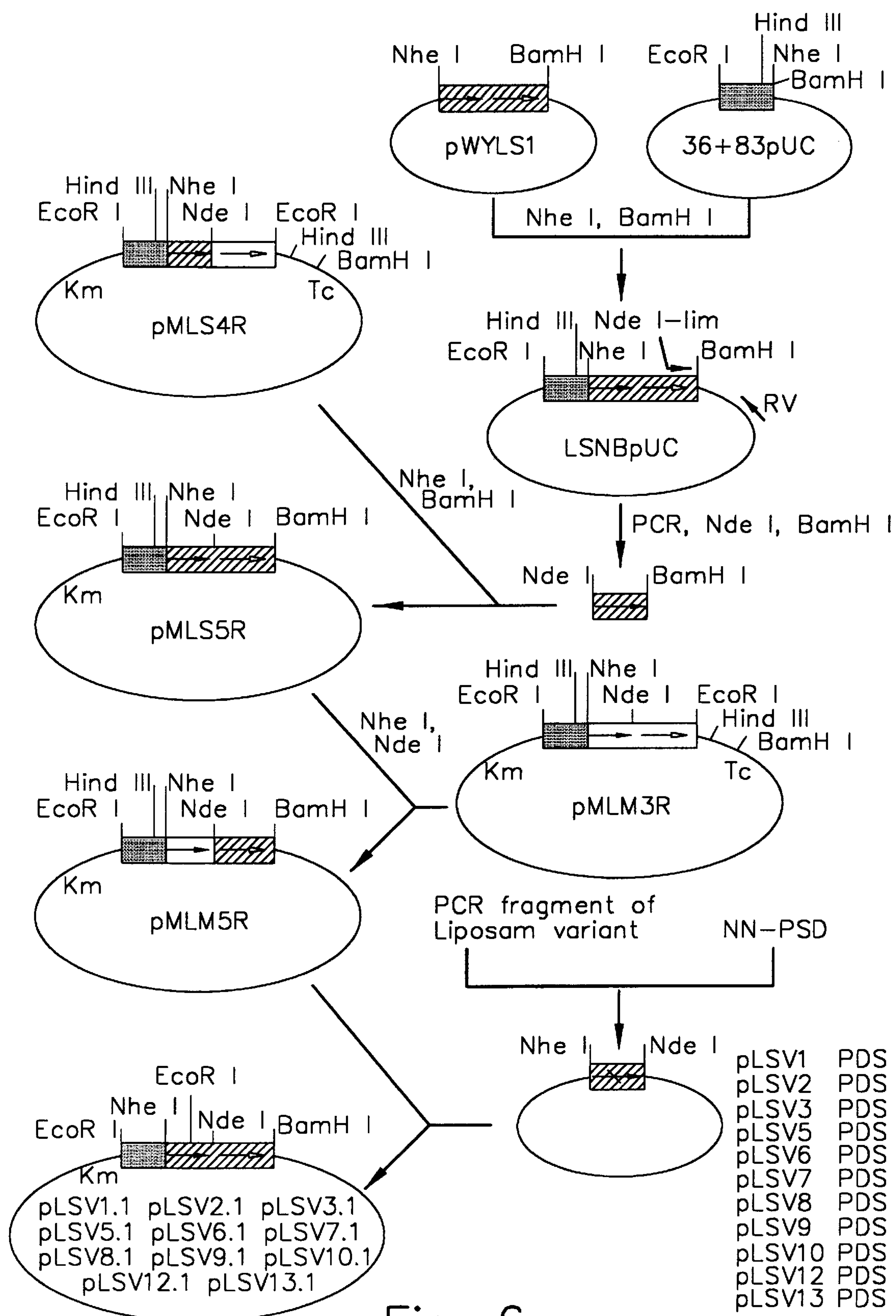
FIG. 6 shows the construction of expression plasmids for Liposam variants based on pMLS5R and pMLM5R.
Figure 7:
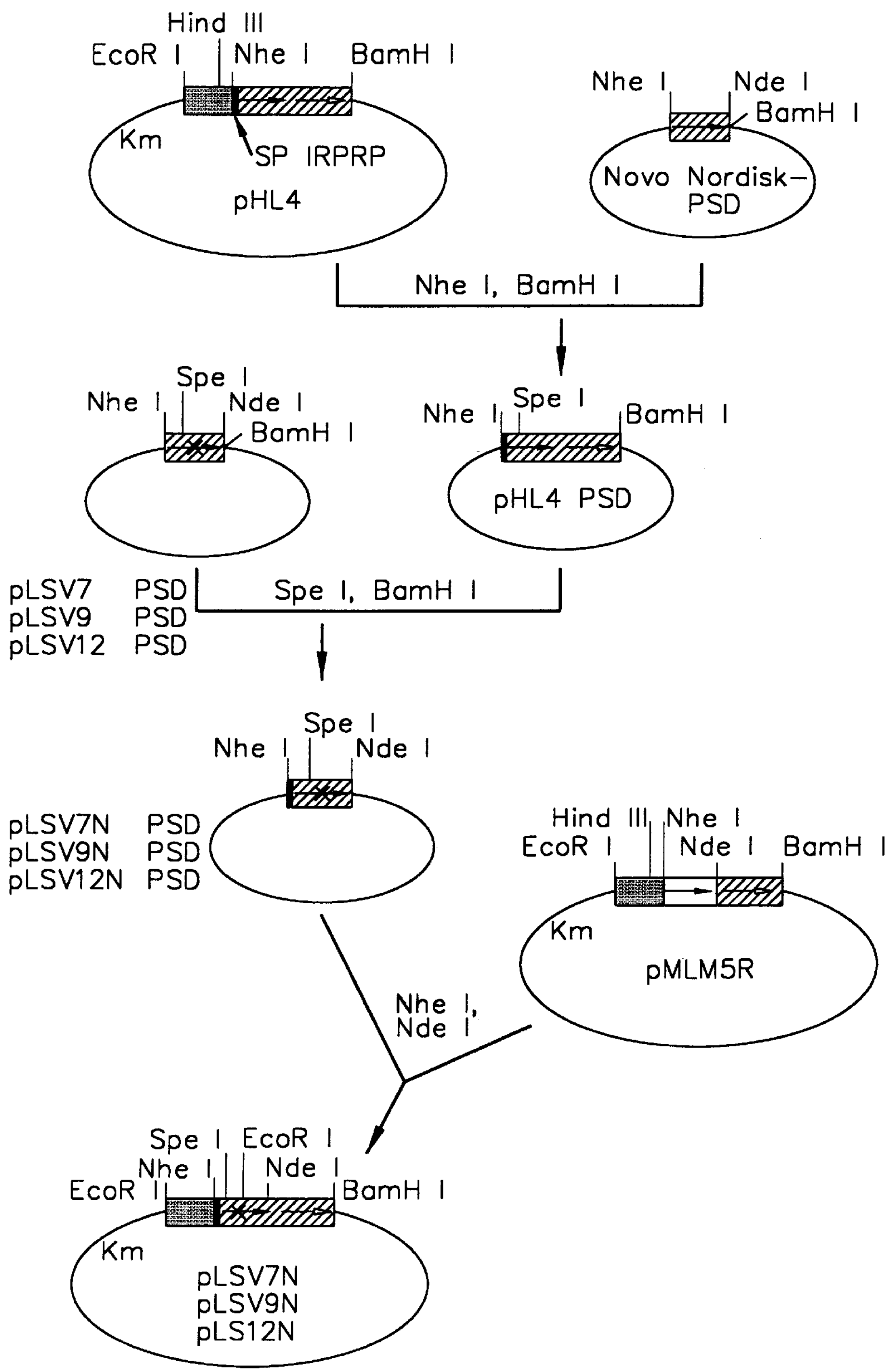
FIG. 7 shows the construction of expression plasmids for N-terminal extension of LSV7, LSV9 and LSV12.
Figure 9:
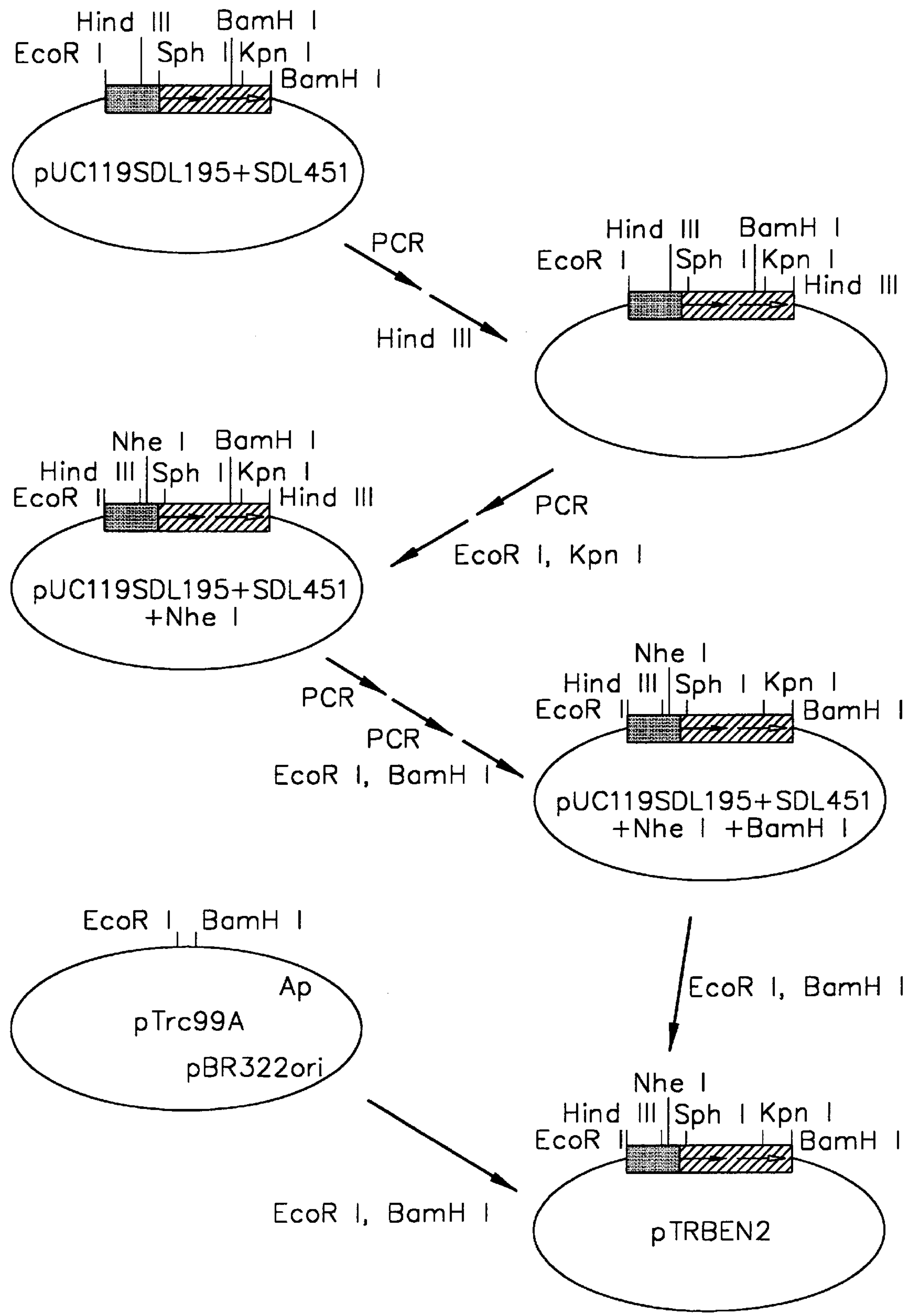
FIG. 9 shows the construction of pTRBEN2.

LMNBpUC is constructed from pUC119SDL195+SDL451 and 36+83pUC, as shown in FIG. 4.

pMES6 is constructed from pMFY42 and pUC119SDL195+SDL451, as shown in FIG. 3.

pMLM3R, an expression vector for the M1 lipase gene (EP 334,462), was prepared as follows: pLMNBpUC was digested with Hind III and the smaller fragment among the obtained 2 fragments was isolated. The fragment was transferred into Hind III site of pMES6. The constructed plasmid was termed pMLM3R.

pUSlim=pUClim2=pUCSlim2 is an *E. coli* expression vector containing phoA signal sequence, synthetic Liposam lim gene and Liposam wild lim gene under the control of araB promoter. The region of araB promoter and signal sequence was amplified with pARA-6D9Fab (Journal of molecular biology (1997) 267, No5, 1247–57) as template. The obtained fragment, whose sequence is shown as SEQ ID NO: 21, was digested with EcoRI and Ncol, then ligated into pUC18.

pUCSam is an *E. coli* expression vector which was constructed from pUSlim. It has phoA signal sequence (the last 71 bases of SEQ ID NO: 21) in front of lim gene.

pUCSam ver.2 is a derivative of pUCSam. The difference is that Liposam starts at site 1 in pUCsam but at site 2 in pUCsam ver.2.

pWYLS1 is an *E. coli* vector containing synthetic Liposam gene and Liposam wild type lim gene under the control of lac promoter, which was constructed by exchanging a NheI-BamHI fragment of the M1 lipase gene and synthetic lim gene in pWYLM vector for a NheI-BamHI fragment of pTRBEN2, as shown in FIG. 9.

pMLS5R, expression vector for Liposam gene including synthetic Liposam gene and Liposam lim gene, is constructed from pMLS4R and LSNBpUC, as shown in FIG. 6. NdeI site is introduced between Liposam gene and Liposam lim gene.

pMLM5R, an expression vector for the M1 lipase gene, constructed from pMLM3R and pMLS5R, including the M1 lipase gene and Liposam lim gene, as shown in FIG. 6.

pHL4 is a Pseudomonas expression vector containing Liposam with N-terminal extension of SPRPRP and lim genes, which was constructed from pHL2 (M1 lipase with N-terminal extension).

pHL4 PSD, constructed from pHL4 and Novo Nordisk-PSD, as shown in FIG. 7.

Figure 10:
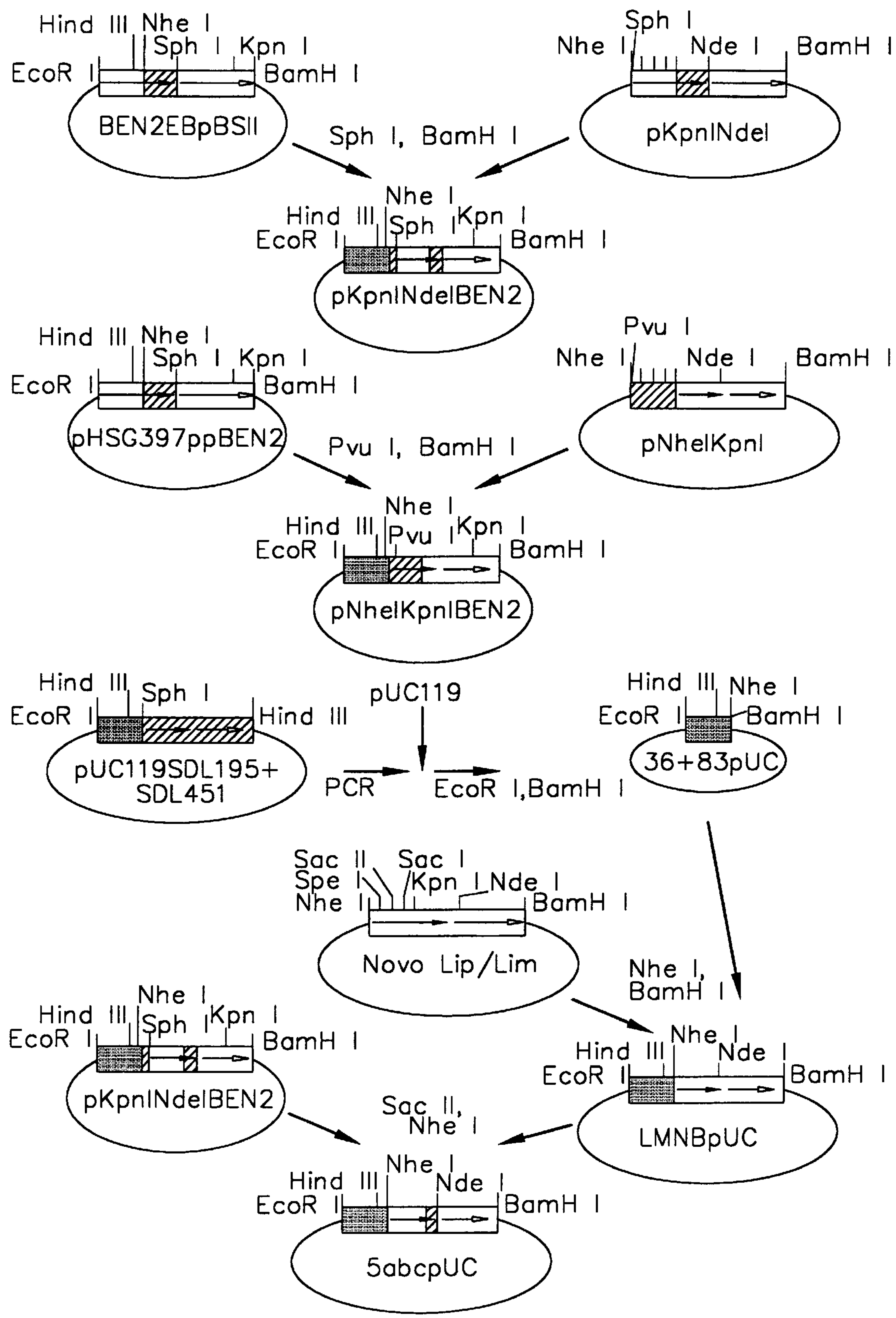
FIG. 10 shows the construction of LMNBpUC.

LMNBpUC is constructed from pUC119SDL195+SDL451 and 36+83pUC. (See FIG. 10).

LSNNBpUC is a plasmid constructed from LMNBPUC, containing SD702 promoter, synthetic Liposam gene and synthetic Lipomax lim gene.

LSNBpUC is a plasmid constructed from pWYLS1, containing SD702 promoter and synthetic Liposam lipase gene and Liposam wild lim gene.

pMLM3R was prepared as follows. pLMNBpUC was digested with Hind III and the smaller fragment among the obtained 2 fragments was isolated. The fragment was transferred into Hind III site of pMES6. The constructed plasmid was termed pMLM3R.

pMLS4R is a Pseudomonas expression vector constructed from pMLM3R (Pseudomonas expression vector for M1 lipase), which is containing a synthetic Liposam gene and synthetic M1 lipase lim gene.

pMLS5R is a Pseudomonas expression vector constructed from pMLS4R. It has Liposam original lim gene.

| Media and substrates | | |
|---|---|---|
| LB medium | | |
| 10 g/L | tryptone | |
| 5 g/L | yeast extract | |
| 5 g/L | NaCl, | |
| pH 7.2 | | |
| 2X LB medium | | |
| 20 g/L | tryptone | |
| 10 g/L | yeast extract | |
| 5 g/L | NaCl, | |
| pH 7.2 | | |
| Additives | | |
| Antibiotic and galactosedes (If required) | | |
| Ampicillin to 100 ~ 250 μg/ml | | |
| Arabinose to 0.5% | | |
| Olive oil assay plate | | |
| Olive oil emulsion (2% P.V.A.: Olive oil = 2:1), | | |
| Brilliant green (Indicator, 0.004%), | | |
| 50 mM glysin buffer pH 10 | | |
| EGTA (final concentration, 1.75 mM) | | |
| PCS solution (final concentration, 4 g/L) | | |
| 8 g/L PCS solution: | | |
| 0.48 g | DOBANOL 25-3 | |
| 0.46 g | DOBANOL 25-7 | |
| 0.42 g | SDS | |
| 1.2 g | $NaBO_3.H_2O$ | |
| glycin buffer, adjusts to 1 L | | |
| C9 medium | | |
| (NH4)2SO4 | 0.4% | |
| K2HPO4 | 1.0 | |
| KH2PO4 | 0.4 | |
| MgSO4.7H2O | 0.3 | (sterilize independently before mixing) |
| CaCl2.2H2O | 0.05 | (sterilize independently before mixing) |
| Na2CO3 | 0.3 | (sterilize independently before mixing) |
| Tween80 | 2.0 | (sterilize independently before mixing) |
| FeSO4.7H2O | 0.03 | (sterilize by filtration) |
| MnSO4.nH2O | 0.005 | (sterilize by filtration) |
| For LDM1 transformants, 20 ppm of kanamycin is added. | | |
| C9 medium is modified as follows in some cases; | | |
| C9 modified A | | |
| (NH4)2SO4 | 0.2% | |
| The rest is the same as C9 | | |
| C9 modified B | | |
| (NH4)2SO4 | 0.2% | |
| Tween80 | 0.2% | |
| rape seed oil | 1% | |
| The rest is the same as C9 | | |
| General primers | | |
| Ara 1550F | SEQ ID NO: 4 | |
| S2640F | SEQ ID NO: 16 | |
| S3020F | SEQ ID NO: 18 | |
| S3000R | SEQ ID NO: 17 | |
| S2560R ver2 | SEQ ID NO: 15 | |
| SamAlf II R | SEQ ID NO: 19 | |
| T7 | SEQ ID NO: 20 | |
| PSD-Xho | SEQ ID NO: 12 | |
| Nheclone | SEQ ID NO: 10 | |

-continued

| Media and substrates | |
|---|---|
| Primes for PCR: | |
| Primer Nde-lim | SEQ ID NO: 9 |
| Primer RV | SEQ ID NO: 14 |

Primers for sequencing:

Primer 702SIG (SEQ ID NO: 3)

Position: SD702 lipase signal sequence, just upstream from mature sequence. Direction: 5' to 3' of Liposam gene.

Primer 2640 (SEQ ID NO: 1)

Position: 220 bp downstream from 5' of Liposam gene. Direction: 5' to 3' of Liposam gene.

Primer 3020 (SEQ ID NO: 2)

Position: 580 bp downstream from 5' of Liposam gene. Direction: 5' to 3' of Liposam gene Primer #3 (SEQ ID NO: 11)

Position: 530 bp downstream from 5' of Liposam gene. Direction: 5' to 3' of Liposam gene.

Methods

*E. coli* transformation for constructing libraries and subcloning are carried out by electroporation (BIO-RAD Gene Pulser).

Plasmid DNAs are prepared by alkaline method or with Qiagen® Plasmid Kit.

DNA fragments are recovered from agarose gel by Suprec™-01(TAKARA) or agarase (NEB).

PCR is carried out by PTC-200 DNA Engine with taq polymerase (Boheringer Manheim) except for gene asembly for gene shuffling mutagenesis.

ABI PRISMTM 310 Genetic Analyzer is used for determination of all the DNA sequences.

Method of primary screening in general

Provide LB containing ampicillin plates with a filter (Cellulose acetate) on the top.

Spread *E.coli* cells containing a parent LIPOSAM lipase and lim gene or a mutated LIPOSAM lipase and lim gene in question on the filter and incubate overnight at 37° C.

Transfer the colonies on the filter to a new LB plate containing ampicillin and 0.4% arabinose and incubate overnight at 25° C.

Transfer the colonies on the filter to an olive oil assay plate containing 4 g/L detergent and 1.75 mM EGTA and incubate overnight at 30° C.

Identify colonies found in step 4) having blue halos.

Isolate the colonies and cultivate them in LB medium.

Recover the plasmids and re-transform into *E.coli.*

Confirm if they are positives or not again through the same process.

Determine their DNA sequence.

*E. coli* liquid cultivation

Inoculate a colony into 3 ml of LB broth containing ampicillin at 37° C. overnight.

Inoculate 1 ml of the seed culture to a shake flask with 100 ml of 2× LB broth containing ampicillin at 37° C. for 5 hours.

Add 0.5 ml of 10% arabinose and 10 μl of emulgen

Cultivate at 25° C. for 3 days.

Transformation of Pseudomonas cell

Pseudomonas mendocina LDM1 is cultivated in L medium at 37° C. overnight. 0.1 ml of the culture is used to inoculate into 10 ml of fresh L medium.

Cells are grown at 37° C. till OD660 reaches to 0.5–0.6 (3–4 hours). Then cells are collected by centrifugation at 4500 rpm for 10 minutes. The cells are washed with sterile water and resuspended in 0.5 ml of sterile water at room temperature. Electroporation apparatus is set to 25 μF, 1000 W, 2.5 kV. Four μg of Plasmid DNA containing Liposam variant gene is added into the cell suspension. The cell suspension with DNA is transferred into an electroporation cuvette (0.4 cm electrode gap) and electric pulse is applied. The pulsed cell suspension is transferred into a sterile falcon tube, added 1.5 ml of L medium, and incubated at 37° C. for 60 minutes with shaking. The cells are plated on L plates containing 20 ppm of kanamycin and the plates are incubated at 37° C. for 1 or 2 days.

Determination of DNA sequence

DNA sequence of Liposam variant gene on the expression plasmid was determined by ABI PRISM TM310 with the primers described in materials and methods.

Plate assay

Transformants of Pseudomonas are streaked on cellulose acetate membrane on L plate containing 20 ppm of kanamycin and grown at 37° C. overnight. The membrane with colonies are transferred onto L plate containing olive oil and brilliant green and incubated at 37° C. for over 6 hours.

Alternative method: Pseudomonas transformants are streaked directly on L plate containing olive oil, brilliant green and 20 ppm of kanamycin and grown at 37° C. overnight.

Culture conditions for small scale culture

For small scale culture of LDM1 transformants C9 medium is used.

Loopfuls of cells are inoculated in 1 ml of C9 medium and cultivated for 17 hours at 37° C. with shaking.

EXAMPLES

Example 1

Construction of Liposam expression vector

In order to increase the lipase expression level, we chose a sugar-inducible vector consisting of the *Salmonella typhimurium* araB promoter and a modified phoA signal sequence (SEQ ID NO: 22). This system is known to allow a high level expression of genes encoding proteins. First, the gene encoding the mature Liposam was inserted under the modified phoA signal sequence (pUCSlim2). The transformant harboring pUCSlim2 showed no lipase activity on olive oil plates. The original signal sequence of Liposam lim gene also was exchanged with the modified phoA signal sequence. The cleavage site of the signal sequence was predicted by the signalP program. Two candidates with high probability were found.

The original signal sequences (having the N-terminal shown in SEQ ID NO: 23) were exchanged with the modified phoA signal sequence at a position between L20 and S21 of SEQ ID NO: 23 (PUCSAM) or between A30 and S31 (PUCSAM ver. 2). The expression level of these transformants are shown as follows:

| plasmid | cleavage site | plate test | liquid culture |
|---|---|---|---|
| pUClim2 | original lim gene | – | 0.0 LU/ml |
| pUCSAM | L20-S21 | + | 0.1 LU/ml |
| pUCSAM ver.2 | A30-S31 | ++ | 7.0 LU/ml |

Example 2

Construction of random mutagenized libraries

LIPOSAM mutagenized libraries of error prone PCR, localized random mutagenesis and gene shuffling in *E.coli* were screened on olive oil assay plates as described below in detail. The obtained positives in the first screening were isolated and sequenced to be found some amino acid substitutions occurred in them.

The fresh *E.coli* positive transformants were cultivated in 2 X LB broth.

Error prone PCR method

PCR was performed under the following condition.

| | |
|---|---|
| 10 μl | 10x reaction buffer (Boehringer Manheim) |
| 10 μl | DMSO |
| 0.1 μl | β-mercapto ethanol |
| 1 μl | primer 101 (100 pmol/μl) |
| 1 μl | primer 127 (100 pmol/μl) |
| 0.2 μl | dATP (100 mM) |
| 0.2 μl | dGTP (100 mM) |
| 1 μl | dCTP (100 mM) |
| 1 μl | dTTP (100 mM) |
| 0.55 μl | $MgCl_2$ (1 M) |
| 5 μl | $MnCl_2$ (100 mM) |
| 1 μl | Taq polymerase (1 U/μl Boehringer Manheim) |
| 1 μl | pUCSAM (10 ng/μl) (template) |
| 67.95 μl | $H_2O$ |
| 94° C. 1 minute, 45° C. 1 minute, 70° C. 4 minutes, by 25 cycles | |

The amplified DNA fragments were isolated from agarose gel and digested with Nhe I and Xho I. The resulting 0.7 kb fragment was ligated into the expression vector pUSlim, which had been digested with the same enzymes previously and transformed into *E. coil* DH12S to make *E. coli* library.

300,000 clones in total were screened on olive oil assay plate as described above.

Localized random mutagenesis

Mutagenic primers (oligonucleotides) were synthesized corresponding to the part of the DNA sequence to be mutagenized. Subsequently, the mutagenic primers were used in PCR reactions with suitable opposite primers. The resulting PCR fragments were purified, digested, cloned into *E.coli* expression vector, pUSlim, and transformed into *E.coli* DH12S.

By using this method, 7 libraries containing from 20,000 to 200,000 clones were prepared. All the constructed libraries were screened on olive oil/PVA assay plates as described above.

Designed Mutagenic oligonucleotide primers are oligonucleotrides 201–209 and 211, shown in SEQ ID NO: 24–33 with doping scheme as follows (numbers refer to bottles shown below):

SEQ ID NO: 24 (Oligonucleotide 201): CCG TAC CAG TAG TCG AC A66 (ANT)57 (A/T)57 775 786 555 (a/T)66 (a/T)57 (a/c)56 (a/c)66 787 (g/c)78 (alt)57 (alt)56 (tVg)58 (a/c)77 G85 68(13) (c/g)78 68(15) (c/g)78 G85 788 775 775 (g/c)66 755 ggc cat ggc ttt tgt c SEQ ID NO: 25 (Oligonucleotide 202): ccg cgt gct tca cTa gt 786 (G/T)57 68(13) 768 (a/T)56 88(16) (c/g)78 (a/T)56 G85 (a/T)56 (a/c)78 (tVg)76 (alc)66 586 88 (15) (glc)67 (a/T)57 (alc)76 775 (a/c)77 (tlg)58 (alc)66 G85 995 G85 786 (g/T)56 acc cag cag gga g SEQ ID NO: 26 (Oligonucleotide 203): gtg agc cag ctc gac act agt (11)55 76(a/t) 67(g/c) 77(t/g) (11)55 957 68(a/t) 68(alt) 56(c/g) 957 78(a/t) (11)57 (11)55 58(a/c) 78(a/t) 76(a/c) 58(a/c) 866 77(g/c) (10)55 66(g/t)(10)55 78(alt) 556 ttg ttc ggt cac ag SEQ ID NO: 27 (Oligonucleotide 204): tgc tcg tga cgg agg cga cca ggt c (a/c)77 (c/g)67 (a/T)56 (a/c)76 (t/g)76 (a/t)56 G85 (g/C)67 (t/g)58 (c/g)78 (a/c)77 (c/g)66 (c/g)66 787 768 787 (a/c)66 755 (a/t)57 788 (a/t)56 88(15) cgg ttt gcc gga gat g SEQ ID NO: 28 (Oligonucleotide 205): cgt ggc cgc ggt tcg ccc gga cct ggt c 76(alc) 866 78(c/A) 56(tVg) 576 58(a/c) 77(tVg) 76(alt) 66(g/t) 656 (10)57 77(tVg) 866 76(glt) 56(g/t) 76(g/t) 758 886 58(a/c) 67(c/g) 957 78(a/t) 66(G/T) gaa ggt agc gca tcc SEQ ID NO: 29 (Oligonucleotide 206): gtc gct gga gct ccc 768 (a/t)57 555 788 (tVg)58 (g/t)57 (alt)76 (g/c)66 (a/t)57 (a/c)66 788 (a/t)56 (tVg)58 (g/c)66 (t/g)76 (alt)57 (a/t)58 (a/c)76 68(16) 775 (a/T)76 768 (a/c)66 88(16) (a/c)77 (a/t)56 68(13) (g/c)67 gat gaa atc cgc cgt c SEQ ID NO: 30 (Oligonucleotide 207): ctt tct gag cgg gag ctc c 576 756 56(c/g) 66(g/t) 957 556 866 68(alt) 77(g/c) 56(g/t) 68(a/t) (11)57 576 68(alt) 558 866 (11)57 77(g/c) 76(a/t) 76(glt) 67(g/c) 886 556 76(glt) 67(g/c) 886 ccg cag ggc gtc ccg ac SEQ ID NO: 31 (Oligonucleotide 208): gcg ggg agg tac c 768 995 768 G85 G85 (g/c)67 (a/t)56 (a/c)66 788 (alt)56 (alt)56 G85 786 (g/c)66 68(16) (G/c)66 G65 (a/t)76 768 (a/c)78 (a/c)77 (g/T)56 (g/c)66 68(13) (a/C)77 gaa gcg cgc gtt gaa g SEQ ID NO: 32 (Oligonucleotide 209): gct gga gcg gta cc 866 66(g/t) 68(a/t) 56(c/g) 556 78(a/t) 68(a/c) 758 66(glt) 576 756 68(a/c) 68(a/t) 68(alt) 77(g/c) 76(a/t)56(c/g) 866 68(alt) 56(c/g) 886 77(g/c) 888 (11)55 76(a/t) 556 758 77(g/c) 68(a/t) gtc ggt cgc tgc agc SEQ ID NO: 33 (Oligonucleotide 210): GTC GGT CGC TGC AGC 866 676 68(G/C) 77(G/T) 587 78(G/T) 58(A/C) 676 758 556 85(17) 676 587 556 656 68(G/C) 756 (11)57 78(A/T) 556 957 56C TTC GGC TTG ACC AGC SEQ ID NO: 34 (Oligonucleotide 211): gaa aaa cag ggc ccg gat cta tgg ctc a (a/t)57 (a/c)66 (alt)76 788 68(15) (alt)57 (g/c)67 788 (tVg)76 68(13) 68(13) (g/c)67 G85 (g/t)56 775 (a/T)56 (a/c)77 768 (g/c)78 68(16) 555 (a/t)58 768 (c/g)78 (a/t)57gcc gaa ggt ctg gtt aac

| | |
|---|---|
| Bottle 5: | 94% A, 2% C, 2% G, 2% T |
| Bottle 6: | 94% C, 2% A, 2% G, 2% T |
| Bottle 7: | 94% G, 2% A, 2% C, 2% T |
| Bottle 8: | 94% T, 2% A, 2% C, 2% G |
| Bottle 9: | 94% C, 3% G, 3% A |
| Bottle 10: | 94% A, 3% G, 3% C |
| Bottle 11: | 94% G, 3% A, 3% C |
| Bottle 12: | 94% C, 6% T |
| Bottle 13: | 94% G, 3% C, 3% T |
| Bottle 14: | 94% G, 6% A |
| Bottle 15: | 94% T, 3% C, 3% G |
| Bottle 16: | 94% C, 3% T, 3% G |
| Bottle 17: | 90% C, 10% T |

Most of the PCR works were carried out under the following condition:

| | |
|---|---|
| 71.45 μl | $H_2O$ |
| 10 μl | 10X reaction buffer (w/o Mg) |
| 0.55 μl | 1 M $MgSO_4$ |
| 10 μl | DMSO |
| 1 μl | Taq polymerase (1 U/μl) |
| 1 μl X 2 | Primers (100 pmol/μl) |
| 1 μl X 4 | dNTPs (100 mM) |
| μl | Template (pUSlim) |
| 94° C. 1 minute, 50° C. 1 minute, 70° C. 4 minutes, by 25 cycles | |

Examples of the combination of primers are shown in the following table.

Combination of primers

| Primer | SEQ ID NO: | Restriction enzyme sites | Targeted region for mutagenesis |
|---|---|---|---|
| 201-202 Nheclone | 24, 25, 10 | Nhe I-Sac I | G2-G27, V28-D54 |
| 202-Ara 1550F | 25, 4 | Bam HI-Spe I | V28-D54 |
| 203-206 | 26, 29 | Spe I-Sac I | E57-N80, R122-S149 |
| Ara 1550F-204 205-S3000R | 4, 27, 28, 17 | BamH I-Sac I | K78-P99, A103-P115 |
| 207-211 | 30, 34 | Sac I-Xho I | S153-F178, L264-L288 |
| S2640F-208 | 16, 31 | Sac I-Xho I | P179-S203, S206-L234 |
| 209-Sam Afl II R | 32, 19 | | |
| 210-SamAfl II R | 19, 33 | Pst I-Afl II | S240-T261 |

Gene shuffling mutagenesis

The method for DNAseI treatment and gene assembly was followed to Stemmer's protocol except some modifications.

Ten pg of pNOVO-PSD was digested by 0.15U of DNaseI in 1 00μl of reaction buffer (50 mM Tris-Cl, pH7.0, 2mM $MgCl_2$) at r.t. for 5 to 8 minutes.

200~400 bp of DNAsed fragments were then recovered and reassembled by PCR under the following condition without primers.

| | |
|---|---|
| 21.8 μl | $H_2O$ |
| 33 μl | 3.3 X reaction buffer |
| 8.8 μl | 25 mM MgOAc |
| 0.4 μl | 1 M $MgCl_2$ |
| 25 μl | 40% PEG |
| 2 μl | rTth polymerease XL (Perkin Elmer) |
| 8 μl | dNTPs (10 mM) |
| 1 μl | Template (>1 μg) |
| 1 | 94° C. 20 sec |
| 2 | 94° C. 15 sec |
| 3 | 45° C. 45 sec |
| 4 | 72° C. 30 sec + 3 sec/cycle |
| 2–4 | 50 cycles |
| 5 | 72° C. 10 min |

The obtained circularized plasmid was purified by CHROMA SIPN+TE-1000 Column (Clontech) and used as template for the second PCR with outer primers.

The PCR work was carried out under the following condition:

| | |
|---|---|
| 62.45 μl | $H_2O$ |
| 10 μl | 10 X reaction buffer (w/o Mg) |
| 0.55 μl | 1 M $MgSO_4$ |
| 10 μl | DMSO |
| 1 μl | Taq polymerase (1 U/μl) |
| 1 μl × 2 | Primers (T7 and PSD-Xho, 100 pmol/μl each) |
| 1 μl × 4 | dNTPs (100 mM) |
| 10 μl | 0.1 μg/μl Template (Reassembled fragment) |
| 94° C. 1 minute, 50° C. 1 minute, 70° C. 4 minutes, by 25 cycles | |

The obtained 0.9 kb fragment was recovered from agarose gel by SUPREC-01 and digested with Nhe I and Xho I. The fragment was gel-purified and ligated into pUSlim, which had been already digested with the same restriction enzymes, and transformed into *E.coli.*

The mutagenesis rate was 3 nucleotide change/Liposam gene (0.9 kb).

Example 3

Determination of sequences of the obtained mutants

The obtained positive mutants were determined their DNA sequences and amino acid sequences. The results were as follows:

| Mutant No# | Amino acid substitutions |
|---|---|
| P22 | T7A |
| P39 | S274F |
| P57 | S3Y and T270I |
| P52 | S130P |
| MLS7-5 | Q278H and G287A |
| MLS9-8 | R277H |

Example 4

Site directed mutation

Construction of expression plasmids for Liposam variants

Figure 5:
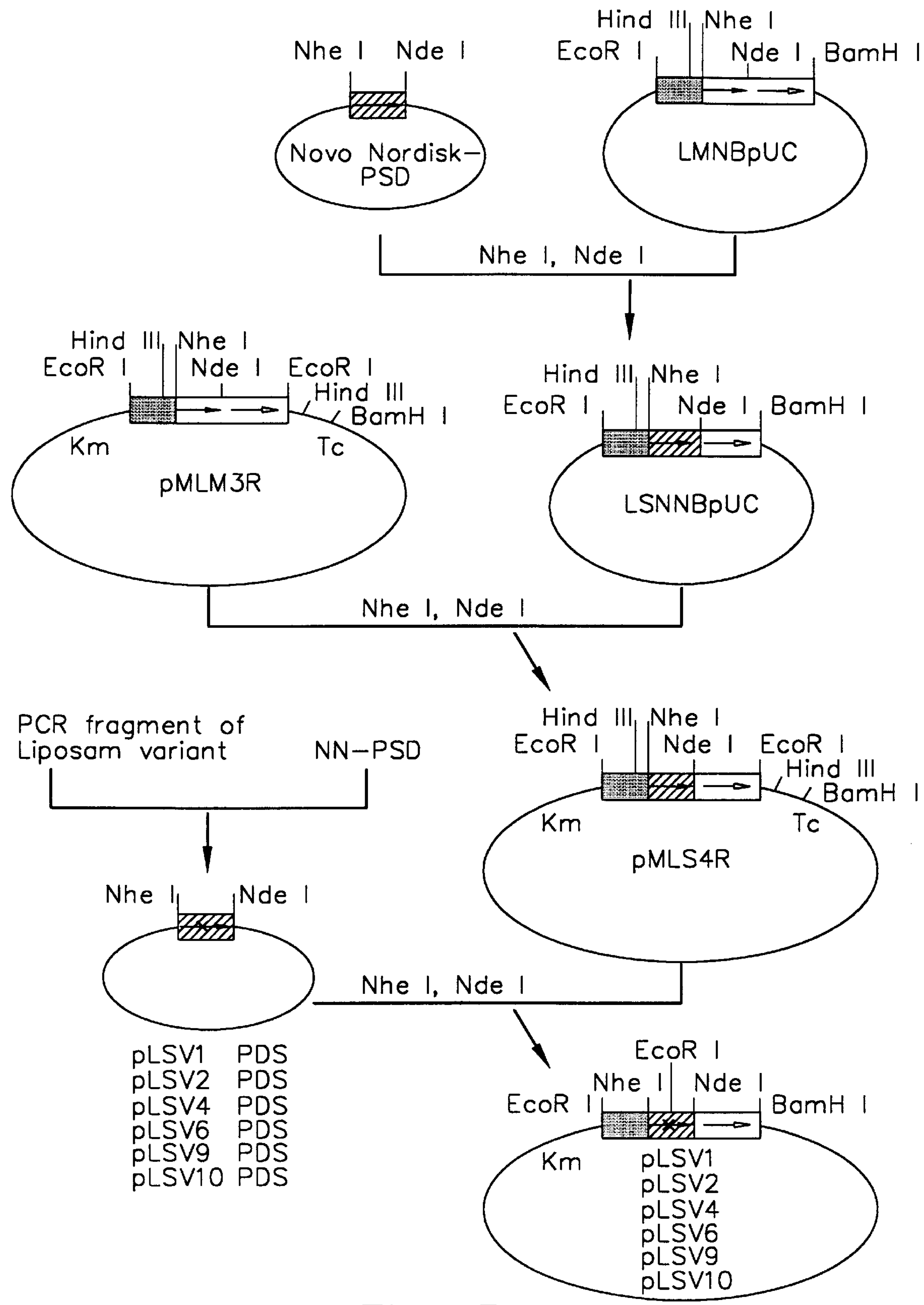
FIG. 5 shows the construction of expression plasmids for Liposam variants based on pMLS4R.

Scheme of construction of expression plasmids for Liposam variants is described in FIG. 5. The plasmids shown in the Table below were constructed based on pMLS4R. DNA sequence of variant gene on the expression plasmid used for transformation was confirmed by genetic analyser. LDM1 was transformed with these plasmids. The transformants were isolated and assayed on olive oil plate containing brilliant green.

Plasmids of Liposam variants based on pMLS4R

| Plasmid name | Variant | plate assay |
|---|---|---|
| pLSV1 | LSV1 | + |
| pLSV2 | LSV2 | + |
| pLSV4 | LSV4 | – |
| pLSV6 | LSV6 | ++ |
| pLSV9 | LSV9 | ++ |
| pLSV10 | LSV10 | – |

Because the expression level of these variants were low, the synthetic lim gene was changed to Liposam origin. New expression plasmids for Liposam variants were constructed based on pMLS5R and pMLM5R. The scheme of construction is described in FIG. 6. DNA sequence of the variant gene on the expression plasmid used for transformation was confirmed by genetic analyzer. LDM1 was transformed with these plasmids. The transformants were isolated and assayed on olive oil plate containing brilliant green. The lipase productivity of LSV2 was improved by changing lim gene to the original Liposam lim gene.

LSV3, LSV4, LSV5, LSV8, LSV10, and LSV11 did not show activity on plates even with the new vector.

Plasmids of Liposam variants based on pMLS5R

| Plasmid name | Variant | plate assay |
|---|---|---|
| pLSV1.1 | LSV1 | + |
| pLSV2.1 | LSV2 | ++ |
| pLSV3.1 | LSV3 | – |
| pLSV5.1 | LSV5 | – |
| pLSV6.1 | LSV6 | ++ |
| pLSV7.1 | LSV7 | ± |
| pLSV8.1 | LSV8 | – |
| pLSV9.1 | LSV9 | ++ |
| pLSV10.1 | LSV10 | – |
| pLSV11.1 | LSV11 | – |
| pLSV12.1 | LSV12 | ++ |
| pLSV13.1 | LSV13 | ++ |

Test tube culture

Each transformant was pre-cultivated on L plate containing 20 ppm of Kanamycin at 37° C. over night. Loopfuls of cells were inoculated into 1ml of C9 medium containing 20 ppm of Km in a test tube and cultivated at 37° C. for 17 hours with shaking. The culture broth was centrifuged and lipase activity in the supernatant was measured. The result is shown in the following Table.

Lipase activity in test tube culture

| Variant | medium | activity (LU/ml) |
|---|---|---|
| wt (pMLS3R) | C9 | 21 |
| | C9 + MSG* | 38 |
| wt (pMLS5R) | C9 | 11 |
| | C9 + MSG | 17 |
| LSV1 (pLSV1.1) | C9 | 0.4 |
| LSV2 (pLSV2.1) | C9 | 0.4 |
| LSV3 (pLSV3.1) | C9 + MSG | 0 |
| LSV5 (pLSV5.1) | C9 + MSG | 0 |
| LSV6 (pLSV6.1) | C9 | 1.2 |
| LSV7 (pLSV7.1) | C9 + MSG | 0 |
| LSV8 (pLSV8.1) | C9 + MSG | 0 |
| LSV9 (pLSV9.1) | C9 | 0.4 |
| LSV11 (pLSV11.1) | C9 + MSG | 0 |
| LSV12 (pLSV12.1) | C9 + MSG | 2.5 |
| LSV13 (pLSV13.1) | C9 + MSG | 1.8 |

0.5% mono sodium glutamate was added to C9

Cultivation in jar fermenter

Because the productivity was lower than wt, the variants described below were cultivated in a jar fermenter.

LSV1
LSV2
LSV6
LSV7
LSV9
LSV12

Assay of Liposam variants

LSV7, LSV9, and LSV12 showed similar performance as wt in detergents. LSV2 and LSV6 showed similar performance as wt at lower detergent concentration range.

Example 5

Construction of new variants of LSV7, LSV9, and LSV12

Combinations of LSV7, LSV9, and LSV12 were constructed. N-terminal extension was also added to these three variants and their combinations.

Figure 8:
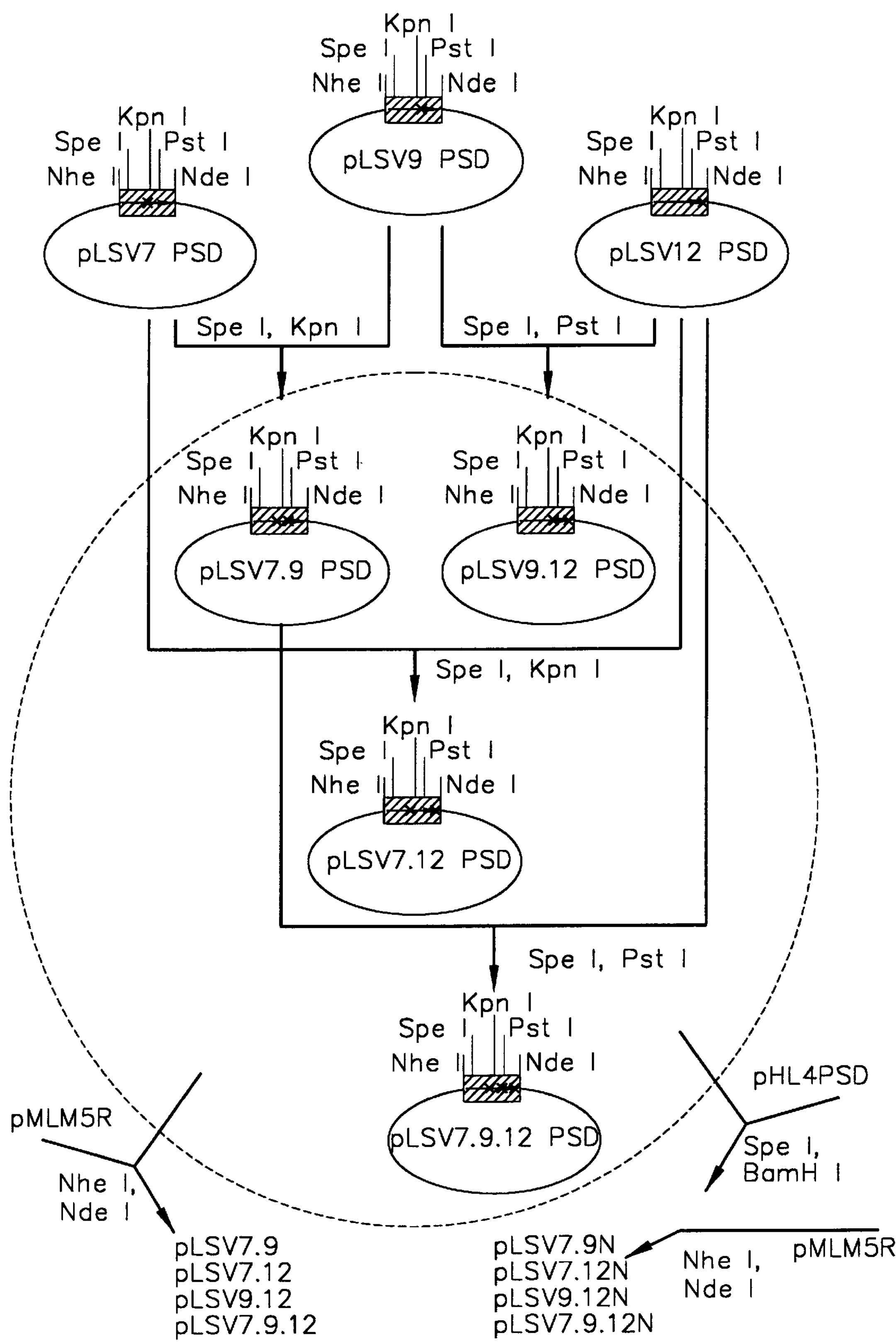
FIG. 8 shows the construction of expression plasmids for combinations of LSV7, LSV9, LSV12 and their N-terminal extensions.

New Liposam variants of the combination of LSV7, LSV9, and LSV12 were constructed by restriction enzyme digestion and ligation. New Liposam variants with of N-terminal extensions of LSV7, LSV9, LSV12 and their combinations were also constructed. The scheme of the construction is shown in FIG. 7 and 8.

Combinations:

LSV7.9
LSV7.12
LSV9.12
LSV7.9.12

N-terminal extensions:

LSV7N
LSV9N
LSV12N
LSV7.9N
LS7.12N
LSV9.12N
LSV7.9.12N

Among these variants, LSV7.12 and LSV7.12N were cultivated at first. The reason was that LSV7 have shown almost the same performance with wt but slightly better than wt in lower detergent concentration range and LSV12 have shown almost the same performance with wt but slightly better than wt in higher detergent concentration range.

Assay of combinations and N-terminal extensions

LSV7.12N showed extremely higher performance than wt while LSV7.12 showed the similar performance with wt.

To investigate LSV7.12N in detail, it was purified by acetone precipitation with ammonium sulfate (20% saturated) and desalted by gel filtration. The precipitate by acetone was dried and resuspended in 50 mM Glycine buffer pH9. The suspension was centrifuged and supernatant was recovered. The supernatant was applied to a gel filtration column (PD-10, Pharmacia). Enzyme was eluted with 50 mM Glycine buffer pH9.

The desalted LSV7.12N was compared with wt. It still showed better performance than wt.

The other N-terminal extensions of the combinations described below were fermented in jars.

LSV9N

LSV12N

LSV9.12N

In general, the lipase productivity of variants including mutation of the seventh region was considerably lower than wt. The other variants were produced sufficiently. LSV9N showed almost the same performance as wt, and LSV9.12N almost the same as LSV12N. We can say that the mutation in the ninth region had no effect for the performance. Therefore, LSV12N became the focus of interest.

Comparison of LSV12N with wild type and HL4

The purified LSV12N was compared with wt and HL4, which is N-terminal extension of wt, in different detergent solutions, Ariel Futur and Super Compact Top (commercial laundry detergent, product of Lion Corp., Japan).

LSV12N was better than wt especially at high detergent concentration range. It was almost the same with HL4 in Ariel but better than HL4 in Top. Further more, LSV12N was compared with LSV7.12N. LSV12N was slightly better than LSV7.12N both in Ariel future and super compact Top.

Conclusion

The mutation in the twelfth region was effective for the improvement of the performance of Liposam in detergent solution. Higher concentration of detergent in- hibits the enzyme activity of LSV12N less than wt. LSV12N seems to be more stable at high detergent concentration.

The structure and plate assay results for the variants prepared by site directed mutagenesis are summarized below:

| Variant name | Modifications | Plate assay |
|---|---|---|
| wt | -1AS, M19V | + |
| LSV1 | -1AS, M19V, F1*, G2*, S3*, S4* | + |

-continued

| Variant name | Modifications | Plate assay |
|---|---|---|
| LSV2 | -1AS, M19V, E61A, Q62E, L64A, T65R | + |
| LSV3 | -1AS, M19V, V67I, E68V, E69P, I70W, V71A, I73*, S74G, K76G, P77G | − |
| LSV4 | -1AS, M19V, A116K, T117V, F120V, I121V, Q123G, V124VL, E126P | − |
| LSV5 | -1AS, M19V, A132G, I133G, L134A, A135N, G136A | − |
| LSV6 | -1AS, M19V, S153N, D154*, T155* | ++ |
| LSV7 | -1AS, M19V, A186SY | + |
| LSV8 | -1AS, M19V, G188A, E189K, G190S, D191T, Y192E, V193VHNVR, V194G, N195H, G196S, V197I | − |
| LSV9 | -1AS, M19V, F228S, A230K | ++ |
| LSV10 | -1AS, M19V, R237V, S240T, R241Y | − |
| LSV11 | -1AS, M19V, R247D, N249S, R251N | − |
| LSV12 | -1AS, M19V, E257A, V258I, Q260H, T261L | ++ |
| LSV13 | -1AS, M19V, L264I, T265R, S266G, I267W, F268*, E269* | ++ |
| LSV7.9 | -1AS, M19V, A186SY, F228S, A230K | − |
| LSV7.12 | -1AS, M19V, A186SY, E257A, V258I, Q260H, T261L | + |
| LSV9.12 | -1AS, M19V, F228S, A230K, E257A, V258I, Q260H, T261L | + |
| LSV7.9.12 | -1AS, M19V, A186SY, F228S, A230K, E257A, V258I, Q260H, T261L | − |
| LSV7N | -1ASPIRPRP, A186SY | |
| LSV9N | -1ASPIRPRP, F228S, A230K | + |
| LSV12N | -1ASPIRPRP, E257A, V258I, Q260H, T261L | + |
| LSV7.9N | -1ASPIRPRP, A186SY, F228S, A230K | + |
| LSV7.12N | -1ASPIRPRP, A186SY, E257A, V258I, Q260H, T261L | + |
| LSV9.12N | -1ASPIRPRP, F228S, A230K, E257A, V258I, Q260H, T261L | + |
| LSV7.9.12N | -1ASPIRPRP, A186SY, F228S, A230K, E257A, V258I, Q260H, T261L | − |
| HL3 | -1ASPIRR, M19V | + |
| HL4 | -1ASPIRPRP, M19V | + |

Example 6

Washing tests

Comparative washing tests were made with the variant lipase LSV12N (described above) and the prior-art lipase Liposam (described in WO 95/06720 and WO 96/27002), using two different detergents. Test swatches soiled with lard and sudan red as indicator were washed at the conditions shown below, and the remission at 460 nm was measured before and after washing. The results are expressed as increase in remission (ΔR).

| Detergent | Ariel Futur | Super Compact Top |
|---|---|---|
| Det. Concentration, g/l | 3.3 | 0.5 |
| Washing time, min. | 20 | 10 |
| Temperature, ° C. | 30 | 30 |
| Water hardness, ° dH | 18 | 3 |
| Lipase dosage, LU/l | 1250 | 5000 |
| ΔR, Liposam | 0 | 0.5 |
| ΔR, LSV12N | 4.8 | 3.5 |

The results clearly show an increased washing performance at typical US and Japanese washing conditions.

What is claimed is:

1. A polypeptide having lipase activity and at least 85% amino acid sequence identity to the mature, wild-type lipase derived from Psuedomonas sp strain SD 705 (FERM BP-4772) and comprising modifications selected from the group consisting of:

a) −1AS, M19V, F228S, and A230K, b) −1AS, M19V, E257A, V2581, Q260H, and T261L, c) −1ASPIRPRP, E257A, V2581, Q260H, and T261L; and d) −1ASPIRPRP, A186SY, E257A, V259I, Q260H, and T261L.

2. A detergent composition comprising a surfactant and 1 the lipase of claim 1.

* * * * *

SEQUENCE LISTING

<160> NUMBER OF SEQ ID NOS: 34

<210> SEQ ID NO 1
<211> LENGTH: 23
<212> TYPE: DNA
<213> ORGANISM: Artificial Sequence
<220> FEATURE:
<223> OTHER INFORMATION: Primer 2640

<400> SEQUENCE: 1
gctgacccag gtggaggaaa tcg 23

<210> SEQ ID NO 2
<211> LENGTH: 19
<212> TYPE: DNA
<213> ORGANISM: Artificial Sequence
<220> FEATURE:
<223> OTHER INFORMATION: Primer 3020

<400> SEQUENCE: 2
cgtggtgaac ggtgtgcgc 19

<210> SEQ ID NO 3
<211> LENGTH: 20
<212> TYPE: DNA
<213> ORGANISM: Artificial Sequence
<220> FEATURE:
<223> OTHER INFORMATION: Primer 702SIG

<400> SEQUENCE: 3
gcctgctcgc cagcggccag 20

<210> SEQ ID NO 4
<211> LENGTH: 23
<212> TYPE: DNA
<213> ORGANISM: Artificial Sequence
<220> FEATURE:
<223> OTHER INFORMATION: Primer Ara1550F

<400> SEQUENCE: 4
gcattagcat ttttgtccat aag 23

<210> SEQ ID NO 5
<211> LENGTH: 21
<212> TYPE: DNA
<213> ORGANISM: Artificial Sequence
<220> FEATURE:
<223> OTHER INFORMATION: Primer IN1

<400> SEQUENCE: 5
gggagctcgc tcctacacga a 21

<210> SEQ ID NO 6
<211> LENGTH: 28
<212> TYPE: DNA
<213> ORGANISM: Artificial Sequence
<220> FEATURE:
<223> OTHER INFORMATION: Primer IN2

<400> SEQUENCE: 6
ggggtaccgg gcgttctcga tggttttt 28

<210> SEQ ID NO 7
<211> LENGTH: 28

-continued

<212> TYPE: DNA
<213> ORGANISM: Artificial Sequence
<220> FEATURE:
<223> OTHER INFORMATION: Primer IN3

<400> SEQUENCE: 7
ggggtacccg tcacgcgctg tcgcgcgc 28

<210> SEQ ID NO 8
<211> LENGTH: 20
<212> TYPE: DNA
<213> ORGANISM: Artificial Sequence
<220> FEATURE:
<223> OTHER INFORMATION: Primer IN4

<400> SEQUENCE: 8
gggcatgcgc gagcaggctg 20

<210> SEQ ID NO 9
<211> LENGTH: 43
<212> TYPE: DNA
<213> ORGANISM: Artificial Sequence
<220> FEATURE:
<223> OTHER INFORMATION: Primer Nde-lim

<400> SEQUENCE: 9
cagtcacagg agatcgatat ccatatgaag ccgctgattt atc 43

<210> SEQ ID NO 10
<211> LENGTH: 40
<212> TYPE: DNA
<213> ORGANISM: Artificial Sequence
<220> FEATURE:
<223> OTHER INFORMATION: Primer Nheclone

<400> SEQUENCE: 10
gacaaaagcc atggccgcta gcttcggctc ctccaactac 40

<210> SEQ ID NO 11
<211> LENGTH: 19
<212> TYPE: DNA
<213> ORGANISM: Artificial Sequence
<220> FEATURE:
<223> OTHER INFORMATION: Primer #3

<400> SEQUENCE: 11
gcgcgcttcc cgcagggcg 19

<210> SEQ ID NO 12
<211> LENGTH: 37
<212> TYPE: DNA
<213> ORGANISM: Artificial Sequence
<220> FEATURE:
<223> OTHER INFORMATION: Primer PSD-Xho

<400> SEQUENCE: 12
tactcaagct cctcgagcat atggatatcg atctcct 37

<210> SEQ ID NO 13
<211> LENGTH: 946
<212> TYPE: DNA
<213> ORGANISM: Artificial Sequence
<220> FEATURE:
<223> OTHER INFORMATION: Synthetic gene PSD

<400> SEQUENCE: 13

-continued

```
gctagcttcg gctcctccaa ctacaccaag acccagtacc cgatcgtgct gacccacggt     60
gttttgggtt ttgactccct gctgggtgtc gactactggt acggtatccc gtccgcgctg    120
cgcaaagatg gtgccacggt ttacgtgacc gaagtgagcc agctcgacac tagtgaagca    180
cgcggtgaac agctgctgac ccaggtggag gaaatcgtgg ccatctccgg caaaccgaaa    240
gtgaacttgt tcggtcacag ccacggcggc ccgaccatcc gctacgtggc cgcggttcgc    300
ccggacctgg tcgcctccgt cacgagcatc ggggccccgc acaagggttc cgcgacggcg    360
gatttcatcc gccaggtgcc ggaaggtagc gcatccgagg cgattctggc cggcatcgtg    420
aacggtttgg gcgcactcat caactttctg agcgggagct ccagcgacac cccgcagaac    480
tccctgggca cgctggagag cctgaattcc gagggcgcag cgcgcttcaa cgcgcgcttc    540
ccgcagggcg tcccgacgag cgcatgcggc gagggcgact acgtggtgaa cggtgtgcgc    600
tactacagct ggagcggtac ctccccgctg accaacgtgc tcgatccgag cgacctcctg    660
ctgggcgcaa cctccctgac cttcggcttt gaagcaaacg atggcctggt cggtcgctgc    720
agctcccgcc tcggtatggt gatccgcgat aactaccgca tgaaccacct cgacgaggtt    780
aaccagacct tcggcttgac cagcattttt gagaccagcc cggtttccgt ctaccgccag    840
caggccaacc gcctgaagaa cgcaggtctg tgatataggc tccacaacca gacaggcctg    900
gcccctcagg ggccagtcac aggagatcga tatccatatg ggatcc                   946
```

<210> SEQ ID NO 14
<211> LENGTH: 17
<212> TYPE: DNA
<213> ORGANISM: Artificial Sequence
<220> FEATURE:
<223> OTHER INFORMATION: Primer RV

<400> SEQUENCE: 14

```
caggaaacag ctatgac                                                    17
```

<210> SEQ ID NO 15
<211> LENGTH: 18
<212> TYPE: DNA
<213> ORGANISM: Artificial Sequence
<220> FEATURE:
<223> OTHER INFORMATION: Primer S2560R

<400> SEQUENCE: 15

```
agaaaacagg gctcgagc                                                   18
```

<210> SEQ ID NO 16
<211> LENGTH: 24
<212> TYPE: DNA
<213> ORGANISM: Artificial Sequence
<220> FEATURE:
<223> OTHER INFORMATION: Primer S2640F

<400> SEQUENCE: 16

```
gctgacccag gtggaggaaa tcgt                                            24
```

<210> SEQ ID NO 17
<211> LENGTH: 28
<212> TYPE: DNA
<213> ORGANISM: Artificial Sequence
<220> FEATURE:
<223> OTHER INFORMATION: Primer S300R

<400> SEQUENCE: 17

```
agctgtagta gcgcacaccg ttcaccac                                        28
```

-continued

<210> SEQ ID NO 18
<211> LENGTH: 20
<212> TYPE: DNA
<213> ORGANISM: Artificial Sequence
<220> FEATURE:
<223> OTHER INFORMATION: Primer S3020F

<400> SEQUENCE: 18
ctgggtgaac ggtgtgcgct 20

<210> SEQ ID NO 19
<211> LENGTH: 20
<212> TYPE: DNA
<213> ORGANISM: Artificial Sequence
<220> FEATURE:
<223> OTHER INFORMATION: Primer SamAlf

<400> SEQUENCE: 19
catccaagct cgccatctgc 20

<210> SEQ ID NO 20
<211> LENGTH: 17
<212> TYPE: DNA
<213> ORGANISM: Artificial Sequence
<220> FEATURE:
<223> OTHER INFORMATION: Primer T7

<400> SEQUENCE: 20
aatacgactc actatag 17

<210> SEQ ID NO 21
<211> LENGTH: 1300
<212> TYPE: DNA
<213> ORGANISM: Artificial Sequence
<220> FEATURE:
<223> OTHER INFORMATION: Fragment used in pUSlim

<400> SEQUENCE: 21
gaattctcta gacttatgac atctttgtgg acacatcatt cactttttat tcacatccgg 60
ccctgaactc gctaggactt gccccggtgc attttttaaa tacccgcgaa aaatagagct 120
gatcgtcaaa tccaacattg cgcccaacgg tcgctatcgg cattcgcgta gtgctaagca 180
gaagtttcgc ctggctgata cgctgatctt cgcgccagct caatacgcta atgcctaact 240
gctggcggaa cagatgtgat aaccgggagg gcgacaggca gacatgctgg gcgacgctgg 300
cgatatcaaa atggctgtcc gccagatggt cgctgatata ctggcaggca tcgcgcacac 360
ggctatccat cggcgggtgc aacgactcat taattaccgc catacgtctg agcaacaact 420
gctccagcag attgatcgcc agtagctcag aatagcgacc ttccccttgc ccggcgctga 480
tgatctgccc gaacagttcg ctgaaatgcg gctggcgcgc ctcgtccggg cggaaaaatc 540
ctgtctgggc aaagattgtc ggccaggtca gccactcctg ccagtaggcg cgaggccgga 600
aataaaccca ctggtgatac cactcgctgg cgtccggatg ccgtccatag tgatgaatct 660
cgcccggcgg aaacaataat atatcgccag gccgacagac aaactgctcg ccattattat 720
taatgacgcc ctctccgcgg atggtcaggt taagaatata tcccttcatg cccaacggac 780
gatcgataaa aaaatccaga tatccattcg cttcaattgg cgtcagcccg gcgaccagat 840
gggcattaaa tgaatatccc ggcaatagcg gatcattttg cgtttcagcc atgatttctc 900 tacccccga tgttcagaga agaaacaaat tgtccatatc gaccaggacg acagagcttc 960

-continued

```
gtctccgca agactttgcg cttgatgaaa gcacgtatca accccgcttg tgaaaagcgc    1020

tttgtaacaa aagcgtacag ttcaggcgat aaaattaagt aacagaagtg tctataacta   1080

tggctggaat gtccacattg aatatttgca cagcgtcaca ctttgcaaag cattagcatt   1140

tttgtccata agattagcgg atcctgcctg acggtttttg ccgcgactct ctactgtttc   1200

tccatacctg tttttctgga tggagtaagc tatgaaacaa agcactattc tactgctgct   1260

cttactgtta ctgctgaccc ctgtgacaaa agccatggcc                         1300


<210> SEQ ID NO 22
<211> LENGTH: 22
<212> TYPE: PRT
<213> ORGANISM: Artificial Sequence
<220> FEATURE:
<223> OTHER INFORMATION: Modified phoA signal sequence

<400> SEQUENCE: 22

Met Lys Gln Ser Thr Ile Leu Leu Leu Leu Leu Leu Leu Leu Leu Thr
 1               5                  10                  15

Pro Val Thr Lys Met Ala
            20


<210> SEQ ID NO 23
<211> LENGTH: 35
<212> TYPE: PRT
<213> ORGANISM: Artificial Sequence
<220> FEATURE:
<223> OTHER INFORMATION: N-terminal found in Example 1

<400> SEQUENCE: 23

Met Lys Pro Leu Ile Tyr Leu Pro Leu Leu Leu Gly Leu Gly Leu Leu
 1               5                  10                  15

Gly Trp His Leu Ser Thr Pro Ala Ser Ser Pro Ser Ser Ala Ser Pro
            20                  25                  30

Ala Pro Pro
        35


<210> SEQ ID NO 24
<211> LENGTH: 114
<212> TYPE: DNA
<213> ORGANISM: Artificial Sequence
<220> FEATURE:
<223> OTHER INFORMATION: Oligonucleotide 201

<400> SEQUENCE: 24

ccgtaccagt agtcgacacc wacwacccac tcaaawccwa cmacmccctc sctwacwack     60

atmccgtact gsctcttsct gtacttccac cascccaagg ccatggcttt tgtc          114


<210> SEQ ID NO 25
<211> LENGTH: 111
<212> TYPE: DNA
<213> ORGANISM: Artificial Sequence
<220> FEATURE:
<223> OTHER INFORMATION: Oligonucleotide 202

<400> SEQUENCE: 25

ccgcgtgctt cactagtctc kacctgcctw acttcsctwa cgtawacmct kccmccatct     60

ttsccwacmc cccamcckat mccgtaccag tactckacac ccagcaggga g             111


<210> SEQ ID NO 26
<211> LENGTH: 107
<212> TYPE: DNA
```

-continued

<213> ORGANISM: Artificial Sequence
<220> FEATURE:
<223> OTHER INFORMATION: Oligonucleotide 203

<400> SEQUENCE: 26
gtgagccagc tcgacactag tgaaccwccs cckgaacacc twctwacsca cctwgacgaa 60
atmctwccma tmtccccsaa acckaaactw aacttgttcg gtcacag 107

<210> SEQ ID NO 27
<211> LENGTH: 107
<212> TYPE: DNA
<213> ORGANISM: Artificial Sequence
<220> FEATURE:
<223> OTHER INFORMATION: Oligonucleotide 204

<400> SEQUENCE: 27
tgctcgtgac ggaggcgacc aggtcmccsc cwacmcckcc wacgtascck atsctmccsc 60
csccctccct ctcmcccaaw accttwactt tcggtttgcc ggagatg 107

<210> SEQ ID NO 28
<211> LENGTH: 112
<212> TYPE: DNA
<213> ORGANISM: Artificial Sequence
<220> FEATURE:
<223> OTHER INFORMATION: Oligonucleotide 205

<400> SEQUENCE: 28
cgtggccgcg gttcgcccgg acctggtccc mtccctmack accatmcckc cwcckcacaa 60
cccktcccck ackcckcatt tcatmccsca cctwcckgaa ggtagcgcat cc 112

<210> SEQ ID NO 29
<211> LENGTH: 115
<212> TYPE: DNA
<213> ORGANISM: Artificial Sequence
<220> FEATURE:
<223> OTHER INFORMATION: Oligonucleotide 206

<400> SEQUENCE: 29
gtcgctggag ctccccctwa caaacttkat kacwccsccw acmcccttwa ckatscckcc 60
wacwatmccc tcccawcccc tmccttcmcc wacctgsccg atgaaatccg ccgtc 115

<210> SEQ ID NO 30
<211> LENGTH: 114
<212> TYPE: DNA
<213> ORGANISM: Artificial Sequence
<220> FEATURE:
<223> OTHER INFORMATION: Oligonucleotide 207

<400> SEQUENCE: 30
ctttctgagc gggagctcca cccacacscc kcacaactcc ctwccsackc twgacaccct 60
waattccgac ccsccwcckc csttcaaccc kccsttcccg cagggcgtcc cgac 114

<210> SEQ ID NO 31
<211> LENGTH: 104
<212> TYPE: DNA
<213> ORGANISM: Artifiicial sequence
<220> FEATURE:
<223> OTHER INFORMATION: Oligonucleotide 208

<400> SEQUENCE: 31
gcggggaggt acccctccac ctgtagtasc cwacmccctt wacwacgtac tcsccctcsc 60
cgcawcccct mctmcckacs ccctgmccga agcgcgcgtt gaag 104

-continued

<210> SEQ ID NO 32
<211> LENGTH: 116
<212> TYPE: DNA
<213> ORGANISM: Artificial Sequence
<220> FEATURE:
<223> OTHER INFORMATION: Oligonucleotide 209

<400> SEQUENCE: 32
gctggagcgg tacctcccck ctwacsaacc twctmcatcc kacccacctm ctwctwccsc 60
cwacstccct wacsttcccs tttgaaccwa accatccsct wgtcggtcgc tgcagc 116

<210> SEQ ID NO 33
<211> LENGTH: 96
<212> TYPE: DNA
<213> ORGANISM: Artificial Sequence
<220> FEATURE:
<223> OTHER INFORMATION: Oligonucleotide 210

<400> SEQUENCE: 33
gtcggtcgct gcagctcccg cctsggkatg gtkatmcgcg ataactaccg catgaaccac 60
ctsgacgagg twaaccagac cttcggcttg accagc 96

<210> SEQ ID NO 34
<211> LENGTH: 121
<212> TYPE: DNA
<213> ORGANISM: Artificial Sequence
<220> FEATURE:
<223> OTHER INFORMATION: Oligonucleotide 211

<400> SEQUENCE: 34
gaaaaacagg gcccggatct atggctcawa cmccwccctt cttwacsccc ttkccctgct 60
gsccgtakac ccawacmccc ctsctctcaa awatcctsct wacgccgaag gtctggttaa 120
c 121